United States Patent
Ferrari

(10) Patent No.: US 7,052,681 B2
(45) Date of Patent: May 30, 2006

(54) COSMETIC COMPOSITION CONTAINING A POLYMER AND A FLUORO OIL

(75) Inventor: Veronique Ferrari, Maisons-Alfort (FR)

(73) Assignee: L'Oréal S.A., Paris (FR)

( * ) Notice: Subject to any disclaimer, the term of this patent is extended or adjusted under 35 U.S.C. 154(b) by 184 days.

(21) Appl. No.: 10/047,987

(22) Filed: Jan. 17, 2002

(65) Prior Publication Data

US 2002/0172696 A1 Nov. 21, 2002

Related U.S. Application Data

(60) Provisional application No. 60/294,980, filed on Jun. 4, 2001.

(30) Foreign Application Priority Data

Jan. 17, 2001 (FR) .......................................... 01 00621

(51) Int. Cl.
*A61K 7/027* (2006.01)
*A61K 7/48* (2006.01)

(52) U.S. Cl. ............................ 424/64; 424/59; 424/61; 424/63; 424/69; 424/70.1; 424/70.7; 424/401

(58) Field of Classification Search ................ 424/401, 424/63, 70.7, 64, 65, 69, 59, 61, 70.1
See application file for complete search history.

(56) References Cited

U.S. PATENT DOCUMENTS

| | | | |
|---|---|---|---|
| 2,379,413 A | 7/1945 | Bradley | |
| 2,450,940 A | 10/1948 | Cowan et al. | |
| 2,463,264 A | 3/1949 | Graenacher | |
| 2,662,068 A | 12/1953 | Floyd | |
| 2,663,649 A | 12/1953 | Winkler | |
| 2,890,097 A | 6/1959 | Coe | |
| 2,962,461 A | 11/1960 | Toussaint et al. | |
| 3,086,914 A | 4/1963 | Soloway ...................... | 167/85 |
| 3,141,787 A | 7/1964 | Goetze et al. | |
| 3,148,125 A | 9/1964 | Strianse et al. | |
| 3,156,572 A | 11/1964 | Carlick et al. | |
| 3,255,082 A | 6/1966 | Barton | |
| 3,341,465 A | 9/1967 | Kaufman et al. | |
| 3,412,115 A | 11/1968 | Floyd et al. | |
| 3,615,289 A | 10/1971 | Felton | |
| 3,645,705 A | 2/1972 | Miller et al. | |
| 3,778,394 A | 12/1973 | Lovald et al. | |
| 3,819,342 A | 6/1974 | Gunerman et al. | |
| 3,857,960 A | 12/1974 | Mackles | |
| 3,926,655 A | 12/1975 | Miles | |
| 3,937,811 A | 2/1976 | Papantoniou et al. | |
| 3,969,087 A | 7/1976 | Saito et al. | |
| 4,049,792 A | 9/1977 | Elsnau | |
| 4,051,159 A | 9/1977 | Tsoucalas et al. | |
| 4,062,819 A | 12/1977 | Mains et al. | |
| RE29,871 E | 12/1978 | Papantoniou et al. | |
| 4,128,436 A | 12/1978 | O'Hara et al. | |
| 4,137,306 A | 1/1979 | Rubino et al. | |
| 4,148,875 A | 4/1979 | Barnett et al. | |
| 4,150,002 A | 4/1979 | Drawert et al. | |
| 4,275,054 A | 6/1981 | Sebag et al. | |
| 4,275,055 A | 6/1981 | Nachtigal et al. | |
| 4,278,658 A | 7/1981 | Hooper et al. | |
| 4,279,658 A | 7/1981 | Harvey et al. | |
| 4,337,298 A | 6/1982 | Karim et al. | |
| 4,341,671 A | 7/1982 | Bolze et al. | |
| 4,376,194 A | 3/1983 | Tanaka et al. | |
| 4,387,090 A | 6/1983 | Bolich, Jr. | |
| 4,438,240 A | 3/1984 | Tanaka et al. | |
| 4,466,936 A | 8/1984 | Schapel | |
| 4,536,405 A | 8/1985 | Nara et al. | |
| 4,552,693 A | 11/1985 | Hussain et al. ............. | 252/522 |
| 4,571,267 A | 2/1986 | Drawert et al. | |
| 4,620,492 A | 11/1986 | Vogg et al. | |
| 4,655,836 A | 4/1987 | Drawert et al. | |
| 4,663,428 A | 5/1987 | Okitu et al. | |
| 4,699,779 A | 10/1987 | Palinczar | |
| 4,712,571 A | 12/1987 | Remz et al. | |
| 4,769,285 A | 9/1988 | Rasmussen | |
| 4,806,338 A | 2/1989 | Smith .......................... | 424/47 |
| 4,806,345 A | 2/1989 | Bhattacharyya .............. | 424/70 |
| 4,820,765 A | 4/1989 | Whyzmuzis | |
| 4,822,601 A | 4/1989 | Goode et al. | |
| 4,871,536 A | 10/1989 | Arraudeau et al. .......... | 424/59 |
| 4,937,069 A | 6/1990 | Shin | |

(Continued)

FOREIGN PATENT DOCUMENTS

| | | |
|---|---|---|
| CA | 2003346 | 5/1990 |
| CA | 1319306 | 6/1993 |
| DE | 38 39 136 A1 | 5/1990 |
| DE | 38 43 892 A1 | 6/1990 |
| DE | 42 08 297 A1 | 9/1993 |

(Continued)

OTHER PUBLICATIONS

Richard J. Lewis, Sr., "Ricinoleic Acid," Hawley's Condensed Chemical Dictionary 927 (13th. 1997).
International Search Report in PCT/US04/01071, dated Feb. 22, 2005.
International Search Report in PCT/US03/41618, dated Mar. 11, 2005.
Bush Boake Allen, Inc., Uniclear Formulations, dated Oct. 13, 1998.
Certified English translation of FR 1 529 329.

(Continued)

*Primary Examiner*—Jyothsna Venkat
(74) *Attorney, Agent, or Firm*—Finnegan, Henderson, Farabow, Garrett & Dunner, LLP

(57) ABSTRACT

The invention relates to a physiologically acceptable composition, especially a cosmetic composition, comprising at least one liquid fatty phase which comprises at least one fluoro oil, wherein the at least one liquid fatty phase is structured with at least one structuring polymer chosen from polyamide polymers of formula (I).

23 Claims, No Drawings

U.S. PATENT DOCUMENTS

| | | |
|---|---|---|
| 4,952,245 A | 8/1990 | Iwano et al. |
| 5,034,219 A | 7/1991 | Deshpande et al. |
| 5,061,289 A | 10/1991 | Clausen et al. |
| 5,069,897 A | 12/1991 | Orr ............................ 424/66 |
| 5,073,364 A | 12/1991 | Giezendanner et al. |
| 5,085,859 A | 2/1992 | Halloran et al. |
| 5,102,656 A | 4/1992 | Kasat |
| 5,186,318 A | 2/1993 | Oestreich et al. ............. 206/37 |
| 5,196,260 A | 3/1993 | Dirschl et al. |
| 5,223,559 A | 6/1993 | Arraudeau et al. |
| 5,272,241 A | 12/1993 | Lucarelli et al. .............. 526/15 |
| 5,290,555 A | 3/1994 | Guthauser et al. |
| 5,302,398 A | 4/1994 | Egidio et al. |
| 5,342,894 A | 8/1994 | Robeson et al. |
| 5,362,482 A | 11/1994 | Yoneyama et al. |
| 5,372,852 A | 12/1994 | Titterington et al. |
| 5,389,363 A | 2/1995 | Snyder et al. |
| 5,472,686 A | 12/1995 | Tsubaki et al. |
| 5,486,431 A | 1/1996 | Tuttle et al. |
| 5,489,431 A | 2/1996 | Ascione et al. |
| 5,500,209 A | 3/1996 | Mendolia et al. |
| 5,505,937 A | 4/1996 | Castrogiovanni et al. |
| 5,510,452 A | 4/1996 | Santhanam ................. 528/291 |
| 5,536,871 A | 7/1996 | Santhanam ................. 560/196 |
| 5,538,718 A | 7/1996 | Aul et al. |
| 5,538,793 A | 7/1996 | Inokuchi et al. |
| 5,540,853 A | 7/1996 | Trinh et al. ................... 510/101 |
| 5,603,925 A | 2/1997 | Ross et al. ..................... 424/65 |
| 5,605,651 A | 2/1997 | Balzer |
| 5,610,199 A | 3/1997 | Cohen et al. |
| 5,612,043 A | 3/1997 | Deprez et al. |
| 5,616,331 A | 4/1997 | Allard et al. |
| 5,618,523 A | 4/1997 | Zysman et al. |
| 5,620,693 A | 4/1997 | Piot et al. |
| 5,628,029 A | 5/1997 | Evoy |
| 5,645,632 A | 7/1997 | Pavlin |
| 5,667,770 A | 9/1997 | Szweda et al. ............... 424/64 |
| 5,679,357 A | 10/1997 | Dubief et al. ................ 424/401 |
| 5,683,817 A | 11/1997 | Kenmochi |
| 5,702,519 A | 12/1997 | Nitta et al. |
| 5,719,255 A | 2/1998 | Heucher et al. |
| 5,747,625 A | 5/1998 | Furukawa et al. |
| 5,750,125 A | 5/1998 | Lahanas et al. |
| 5,750,127 A | 5/1998 | Rokitowski |
| 5,750,489 A | 5/1998 | Garcia et al. |
| 5,769,902 A | 6/1998 | Samain |
| 5,780,517 A | 7/1998 | Cohen et al. |
| 5,783,657 A | 7/1998 | Pavlin et al. |
| 5,800,816 A | 9/1998 | Brieva et al. ................. 424/63 |
| 5,807,968 A | 9/1998 | Heinrich et al. |
| 5,830,444 A | 11/1998 | Miguel |
| 5,830,483 A | 11/1998 | Seidel et al. |
| 5,837,223 A | 11/1998 | Barone et al. |
| 5,849,275 A | 12/1998 | Calello et al. |
| 5,849,278 A | 12/1998 | Piot et al. |
| 5,849,333 A | 12/1998 | Nordhauser et al. |
| 5,851,517 A | 12/1998 | Mougin et al. |
| 5,857,903 A | 1/1999 | Ramspeck et al. |
| 5,858,338 A | 1/1999 | Piot et al. |
| 5,866,149 A | 2/1999 | Piot et al. |
| 5,871,764 A | 2/1999 | Diaz et al. |
| 5,874,069 A | 2/1999 | Mendolia et al. ............. 424/65 |
| 5,882,363 A | 3/1999 | Spaulding et al. |
| 5,891,424 A | 4/1999 | Bretzler |
| 5,897,869 A | 4/1999 | Roulier et al. ............... 424/401 |
| 5,902,592 A | 5/1999 | Bara et al. |
| 5,908,631 A | 6/1999 | Arnaud et al. |
| 5,911,974 A | 6/1999 | Brieva et al. ................. 424/64 |
| 5,919,441 A | 7/1999 | Mendolia et al. ......... 424/78.08 |
| 5,925,337 A | 7/1999 | Arraudeau et al. |
| 5,945,095 A | 8/1999 | Mougin et al. |
| 5,945,112 A | 8/1999 | Flynn et al. |
| 5,959,009 A | 9/1999 | Konik et al. ................. 524/261 |
| 5,961,998 A | 10/1999 | Arnaud et al. |
| 5,965,112 A | 10/1999 | Brieva et al. ................. 424/64 |
| 5,972,095 A | 10/1999 | Graves et al. |
| 5,972,354 A | 10/1999 | de la Poterie et al. |
| 5,972,359 A | 10/1999 | Sine et al. |
| 5,976,514 A | 11/1999 | Guskey et al. |
| 5,981,680 A | 11/1999 | Petroff et al. |
| 5,985,298 A | 11/1999 | Brieva et al. |
| 5,993,787 A | 11/1999 | Sun et al. |
| 5,998,570 A * | 12/1999 | Pavlin et al. ................ 528/310 |
| 6,001,980 A | 12/1999 | Borzo et al. |
| 6,004,567 A | 12/1999 | Marchi-Lemann et al. |
| 6,007,799 A | 12/1999 | Lee et al. |
| 6,019,962 A | 2/2000 | Rabe et al. |
| 6,036,947 A | 3/2000 | Barone et al. |
| 6,045,782 A | 4/2000 | Krog et al. |
| 6,045,823 A | 4/2000 | Vollhardt et al. |
| 6,051,216 A | 4/2000 | Barr et al. ................. 424/78.35 |
| 6,054,517 A | 4/2000 | Spaulding et al. |
| 6,060,072 A | 5/2000 | Konik et al. ................. 424/401 |
| 6,063,398 A | 5/2000 | Gueret |
| 6,066,328 A | 5/2000 | Ribier et al. |
| 6,074,654 A | 6/2000 | Drechsler et al. ........... 424/401 |
| 6,103,249 A | 8/2000 | Roulier et al. .............. 424/401 |
| 6,106,820 A | 8/2000 | Morrissey et al. |
| 6,111,055 A | 8/2000 | Berger et al. |
| 6,156,325 A | 12/2000 | Farer et al. ................. 424/401 |
| 6,156,804 A | 12/2000 | Chevalier et al. |
| 6,165,454 A | 12/2000 | Patel et al. |
| 6,165,971 A | 12/2000 | Oppenlander et al. |
| 6,171,347 B1 | 1/2001 | Kunz et al. |
| 6,177,523 B1 | 1/2001 | Reich et al. ................. 525/459 |
| 6,180,117 B1 | 1/2001 | Berthiaume et al. |
| 6,180,123 B1 | 1/2001 | Mondet |
| 6,190,673 B1 | 2/2001 | Guskey et al. ............. 424/401 |
| 6,197,100 B1 | 3/2001 | Melbouci |
| 6,203,780 B1 * | 3/2001 | Arnaud et al. ................ 424/61 |
| 6,203,807 B1 | 3/2001 | Lemann |
| 6,214,326 B1 | 4/2001 | Dupuis |
| 6,214,329 B1 | 4/2001 | Brieva et al. |
| 6,221,389 B1 | 4/2001 | Cannell et al. |
| 6,224,851 B1 * | 5/2001 | Bara ........................ 424/59 |
| 6,242,509 B1 | 6/2001 | Berger et al. |
| 6,251,375 B1 | 6/2001 | Bara |
| 6,251,409 B1 | 6/2001 | Hegyi et al. |
| 6,254,876 B1 | 7/2001 | de la Poterie et al. |
| 6,254,877 B1 | 7/2001 | De La Poterie et al. |
| 6,264,933 B1 | 7/2001 | Bodelin et al. |
| 6,268,466 B1 | 7/2001 | MacQueen et al. |
| 6,280,846 B1 | 8/2001 | Darby et al. |
| 6,287,552 B1 | 9/2001 | Tournilhac et al. |
| 6,325,994 B1 | 12/2001 | Collin et al. |
| 6,348,563 B1 | 2/2002 | Fukuda et al. |
| 6,372,235 B1 | 4/2002 | Livoreil et al. |
| 6,376,078 B1 | 4/2002 | Inokuchi |
| 6,383,502 B1 | 5/2002 | Dunshee et al. |
| 6,399,080 B1 * | 6/2002 | Bara ........................ 424/401 |
| 6,399,081 B1 | 6/2002 | Nakanishi et al. |
| 6,402,408 B1 | 6/2002 | Ferrari |
| 6,423,306 B1 | 7/2002 | Caes et al. |
| 6,423,324 B1 | 7/2002 | Murphy et al. |
| 6,428,773 B1 | 8/2002 | Oko et al. |
| 6,432,391 B1 | 8/2002 | Bara |
| 6,447,759 B1 | 9/2002 | Noguchi et al. |
| 6,469,131 B1 | 10/2002 | Lawson et al. |
| 6,475,500 B1 | 11/2002 | Vatter et al. |
| 6,479,686 B1 | 11/2002 | Nakanishi et al. |
| 6,482,400 B1 | 11/2002 | Collin |

| | | | | | | |
|---|---|---|---|---|---|---|
| 6,491,931 | B1 | 12/2002 | Collin | EP | 0 749 746 A1 | 12/1996 |
| 6,497,861 | B1 | 12/2002 | Wang et al. | EP | 0 749 747 A1 | 12/1996 |
| 6,506,716 | B1 | 1/2003 | Delplancke et al. | EP | 0 749 748 A1 | 12/1996 |
| 6,649,173 | B1 * | 11/2003 | Arnaud et al. ............ 424/401 | EP | 0 775 483 A1 | 5/1997 |
| 6,682,748 | B1 | 1/2004 | De La Poterie et al. | EP | 0 797 976 A2 | 10/1997 |
| 6,726,917 | B1 | 4/2004 | Kanji et al. | EP | 0 820 764 A1 | 1/1998 |
| 6,749,173 | B1 | 6/2004 | Heiling | EP | 0 847 752 A1 | 6/1998 |
| 6,761,881 | B1 | 7/2004 | Bara | EP | 0 877 063 B1 | 11/1998 |
| 6,875,245 | B1 | 4/2005 | Pavlin | EP | 0 879 592 A2 | 11/1998 |
| 2001/0014312 | A1 | 8/2001 | Nakanishi et al. | EP | 0 887 073 A1 | 12/1998 |
| 2001/0014313 | A1 | 8/2001 | Roulier et al. | EP | 0 923 928 A1 | 6/1999 |
| 2001/0028887 | A1 | 10/2001 | Douin et al. | EP | 0 925 780 A1 | 6/1999 |
| 2001/0031280 | A1 | 10/2001 | Ferrari et al. | EP | 0 928 608 A2 | 7/1999 |
| 2001/0033846 | A1 | 10/2001 | Roulier et al. | EP | 0 930 058 B1 | 7/1999 |
| 2002/0044918 | A1 | 4/2002 | Bara | EP | 0 930 060 A1 | 7/1999 |
| 2002/0058053 | A1 | 5/2002 | Nakanishi et al. | EP | 0 943 340 A1 | 9/1999 |
| 2002/0081323 | A1 | 6/2002 | Nakanishi et al. | EP | 0 958 804 A2 | 11/1999 |
| 2002/0102225 | A1 | 8/2002 | Hess et al. | EP | 0 958 805 A2 | 11/1999 |
| 2002/0107314 | A1 | 8/2002 | Pinzon et al. | EP | 0 958 811 A1 | 11/1999 |
| 2002/0111330 | A1 | 8/2002 | Pinzon et al. | EP | 0 959 066 A2 | 11/1999 |
| 2002/0114771 | A1 | 8/2002 | Nakanishi | EP | 0 959 091 A1 | 11/1999 |
| 2002/0114773 | A1 | 8/2002 | Kanji et al. | EP | 0 976 390 A1 | 2/2000 |
| 2002/0119171 | A1 | 8/2002 | Gruning et al. | EP | 0 984 025 A2 | 3/2000 |
| 2002/0120036 | A1 | 8/2002 | Pinzon et al. | EP | 1 002 514 A1 | 5/2000 |
| 2002/0122781 | A1 | 9/2002 | Pinzon et al. | EP | 1 031 342 A1 | 8/2000 |
| 2002/0131947 | A1 | 9/2002 | Nakanishi | EP | 1 048 282 A1 | 11/2000 |
| 2002/0141958 | A1 | 10/2002 | Maio et al. | EP | 1 053 742 A1 | 11/2000 |
| 2002/0150602 | A1 | 10/2002 | Livoreil et al. | EP | 1 062 944 A1 | 12/2000 |
| 2002/0159964 | A1 | 10/2002 | Nakanishi et al. | EP | 1 062 959 A1 | 12/2000 |
| 2002/0168335 | A1 | 11/2002 | Collin | EP | 1 064 919 A1 | 1/2001 |
| 2002/0172696 | A1 | 11/2002 | Ferrari | EP | 1 064 920 A1 | 1/2001 |
| 2002/0189030 | A1 | 12/2002 | Collin | EP | 1 066 814 A1 | 1/2001 |
| 2002/0192168 | A1 | 12/2002 | Blin et al. | EP | 1 068 854 A1 | 1/2001 |
| 2003/0012764 | A1 | 1/2003 | Collin | EP | 1 068 855 A1 | 1/2001 |
| 2003/0026772 | A1 | 2/2003 | Jager-Lezer et al. | EP | 1 068 856 A1 | 1/2001 |
| 2003/0044367 | A1 | 3/2003 | Simon et al. | EP | 1 086 945 A1 | 3/2001 |
| 2003/0086883 | A1 | 5/2003 | Feng et al. | EP | 1 090 627 A1 | 4/2001 |
| 2003/0147837 | A1 | 8/2003 | Cavazzuti et al. | EP | 1 095 959 A2 | 5/2001 |
| 2003/0161807 | A1 | 8/2003 | Lemann | EP | 1 114 636 A1 | 7/2001 |
| 2003/0161848 | A1 | 8/2003 | Ferrari et al. | EP | 1 213 011 A1 | 6/2002 |
| 2003/0185780 | A1 | 10/2003 | Ferrari et al. | EP | 1 213 316 A2 | 6/2002 |
| 2003/0198613 | A1 | 10/2003 | Feng et al. | FR | 1 529 329 | 5/1968 |
| 2004/0013625 | A1 | 1/2004 | Kanji | FR | 2 232 303 | 1/1975 |
| 2004/0028636 | A1 | 2/2004 | Collin | FR | 2 674 126 | 9/1992 |
| 2004/0042980 | A1 | 3/2004 | Kanji et al. | FR | 2 785 179 | 5/2000 |
| 2004/0086478 | A1 | 5/2004 | Ferrari | FR | 2 796 270 | 1/2001 |
| 2004/0091510 | A1 | 5/2004 | Feng et al. | FR | 2 796 271 | 1/2001 |
| 2004/0126401 | A1 | 7/2004 | Collin | FR | 2 796 272 | 1/2001 |
| 2004/0166076 | A1 | 8/2004 | Ferrari et al. | FR | 2 796 273 | 1/2001 |
| 2004/0166133 | A1 | 8/2004 | Cavazzuti et al. | FR | 2 796 276 | 1/2001 |
| | | | | FR | 2 802 806 | 6/2001 |
| | | FOREIGN PATENT DOCUMENTS | | FR | 2 804 017 | 7/2001 |
| DE | | 42 34 886 A1 | 4/1994 | FR | 2 804 018 | 7/2001 |
| DE | | 195 43 988 A | 5/1997 | FR | 2 810 562 | 12/2001 |
| DE | | 195 43 988 A1 | 5/1997 | FR | 2 811 225 | 1/2002 |
| DE | | 197 07 309 A1 | 8/1998 | FR | 2 811 552 | 1/2002 |
| DE | | 197 50 246 A1 | 5/1999 | FR | 2 816 506 | 5/2002 |
| DE | | 199 51 010 A1 | 4/2001 | FR | 2 817 739 | 6/2002 |
| EP | | 0 169 997 B1 | 2/1986 | FR | 2 817 740 | 6/2002 |
| EP | | 0 295 886 B1 | 12/1988 | FR | 2 817 743 | 6/2002 |
| EP | | 0 370 470 B1 | 5/1990 | FR | 2 819 399 | 7/2002 |
| EP | | 0 374 332 A1 | 6/1990 | FR | 2 819 400 | 7/2002 |
| EP | | 0 412 710 B1 | 2/1991 | FR | 2 819 402 | 7/2002 |
| EP | | 0 444 633 A2 | 9/1991 | GB | 1 117 129 | 6/1968 |
| EP | | 0 557 196 A1 | 8/1993 | GB | 1 194 901 | 6/1970 |
| EP | | 0 602 905 B1 | 6/1994 | GB | 1 194 902 | 6/1970 |
| EP | | 0 609 132 B1 | 8/1994 | GB | 1 220 069 | 1/1971 |
| EP | | 0 623 670 A2 | 11/1994 | GB | 1 273 004 | 5/1972 |
| EP | | 0 628 582 B1 | 12/1994 | GB | 1 444 204 | 7/1976 |
| EP | | 0 673 642 B1 | 9/1995 | GB | 2 014 852 | 9/1979 |
| EP | | 0 708 114 A1 | 4/1996 | GB | 2 021 411 A | 12/1979 |

| | | |
|---|---|---|
| GB | 2 147 305 A | 5/1985 |
| GB | 2 196 978 A | 5/1988 |
| JP | 50/58242 | 5/1975 |
| JP | 53/043577 | 4/1978 |
| JP | 56/123909 | 9/1981 |
| JP | 56/166276 | 12/1981 |
| JP | 61/065809 | 4/1986 |
| JP | 62/061911 | 3/1987 |
| JP | 2/127568 | 5/1990 |
| JP | 02/200612 | 8/1990 |
| JP | 2/216279 | 8/1990 |
| JP | 3/014683 | 1/1991 |
| JP | 04/346909 | 12/1992 |
| JP | 7/179795 | 7/1995 |
| JP | 7/267827 | 10/1995 |
| JP | 8/225316 | 9/1996 |
| JP | 9/20631 | 1/1997 |
| JP | 09/255560 | 9/1997 |
| JP | 9/295922 | 11/1997 |
| JP | 10/007527 | 1/1998 |
| JP | 10/120903 | 5/1998 |
| JP | 10/212213 | 8/1998 |
| JP | 10/259344 | 9/1998 |
| JP | 11/106216 | 4/1999 |
| JP | 11/335228 | 12/1999 |
| JP | 11/335242 | 12/1999 |
| JP | 11/335254 | 12/1999 |
| JP | 2000038314 A | 2/2000 |
| JP | 2000038316 A | 2/2000 |
| JP | 2000038317 A | 2/2000 |
| JP | 2000038321 A | 2/2000 |
| JP | 2000086427 A | 3/2000 |
| JP | 2000086429 A | 3/2000 |
| JP | 2000086438 A | 3/2000 |
| WO | WO 86/04916 | 8/1986 |
| WO | WO 87/03783 | 7/1987 |
| WO | WO 91/12793 | 9/1991 |
| WO | WO 93/21763 | 11/1993 |
| WO | WO 93/23008 | 11/1993 |
| WO | WO 94/18261 | 8/1994 |
| WO | WO 95/15741 | 6/1995 |
| WO | WO 95/24887 | 9/1995 |
| WO | WO 95/33000 | 12/1995 |
| WO | WO 96/15761 | 5/1996 |
| WO | WO 96/40044 | 12/1996 |
| WO | WO 97/17057 | 5/1997 |
| WO | WO 97/36573 | 10/1997 |
| WO | WO 98/17243 | 4/1998 |
| WO | WO 98/17705 | 4/1998 |
| WO | WO 98/22078 | 5/1998 |
| WO | WO 98/27162 | 6/1998 |
| WO | WO 98/42298 | 10/1998 |
| WO | WO 98/47470 | 10/1998 |
| WO | WO 98/52534 | 11/1998 |
| WO | WO 98/58623 | 12/1998 |
| WO | WO 99/24002 | 5/1999 |
| WO | WO 00/27350 | 5/2000 |
| WO | WO 00/40216 | 7/2000 |
| WO | WO 00/61080 | 10/2000 |
| WO | WO 00/61081 | 10/2000 |
| WO | WO 00/74519 A2 | 12/2000 |
| WO | WO 01/51020 A1 | 7/2001 |
| WO | WO 01/52799 A1 | 7/2001 |
| WO | WO 01/97758 A2 | 12/2001 |
| WO | WO 01/97773 A1 | 12/2001 |
| WO | WO 02/03932 A2 | 1/2002 |
| WO | WO 02/03935 A2 | 1/2002 |
| WO | WO 02/03950 A2 | 1/2002 |
| WO | WO 02/03951 A2 | 1/2002 |
| WO | WO 02/47605 A2 | 6/2002 |
| WO | WO 02/47608 A2 | 6/2002 |
| WO | WO 02/47619 A2 | 6/2002 |
| WO | WO 02/47620 A2 | 6/2002 |
| WO | WO 02/47622 A2 | 6/2002 |
| WO | WO 02/47627 A1 | 6/2002 |
| WO | WO 02/47629 A1 | 6/2002 |
| WO | WO 02/47630 A1 | 6/2002 |
| WO | WO 02/47658 A2 | 6/2002 |
| WO | WO 02/49583 A1 | 6/2002 |
| WO | WO 02/49601 A1 | 6/2002 |
| WO | WO 02/055030 A2 | 7/2002 |
| WO | WO 02/055031 A1 | 7/2002 |
| WO | WO 02/056845 A1 | 7/2002 |
| WO | WO 02/056847 A1 | 7/2002 |
| WO | WO 02/056848 A1 | 7/2002 |
| WO | WO 02/092047 A1 | 11/2002 |
| WO | WO 02/092663 A1 | 11/2002 |
| WO | WO 02/102322 A2 | 12/2002 |

OTHER PUBLICATIONS

English language DERWENT abstract of DE 42 08 297.
English language DERWENT abstract of DE 195 43 988.
English language DERWENT abstract of DE 197 07 309.
English language DERWENT abstract of DE 197 50 246.
English language DERWENT abstract of DE 199 51 010.
English language DERWENT abstract of DE 38 43 892.
English language DERWENT abstract of DE 38 39 136.
English language DERWENT abstract of DE 42 34 886.
English language DERWENT abstract of EP 0 169 997 B1.
English language DERWENT abstract of EP 0 557 196 A1.
English language DERWENT abstract of EP 0 609 132.
English language DERWENT abstract of EP 0 749 746 A1.
English language DERWENT abstract of EP 0 749 747 A1.
English language DERWENT abstract of EP 0 749 748.
English language DERWENT abstract of EP 0 775 483 A1.
English language DERWENT abstract of EP 0 820 764 A1.
English language DERWENT abstract of EP 0 847 752.
English language DERWENT abstract of EP 0 879 592 A2.
English language DERWENT abstract of EP 0 887 073 A1.
English language DERWENT abstract of EP 0 923 928 A1.
English language DERWENT abstract of EP 0 925 780 A1.
English language DERWENT abstract of EP 0 930 058 B1.
English language DERWENT abstract of EP 0 930 058 B1.
English language DERWENT abstract of EP 0 930 060 A1.
English language DERWENT abstract of EP 0 943 340 A1.
English language DERWENT abstract of EP 0 958 811 A1.
English language DERWENT abstract of EP 0 959 066 A2.
English language DERWENT abstract of EP 0 959 091 A1.
English language DERWENT abstract of EP 0 976 390 A1.
English language DERWENT abstract of EP 0 984 025 A2.
English language DERWENT abstract of EP 1 002 514.
English language DERWENT abstract of EP 1 031 342 A1.
English language DERWENT abstract of EP 1 048 282 A1.
English language DERWENT abstract of EP 1 053 742.
English language DERWENT abstract of EP 1 064 919.
English language DERWENT abstract of EP 1 064 920.
English language DERWENT abstract of EP 1 066 814.
English language DERWENT abstract of EP 1 068 854 A1.
English language DERWENT abstract of EP 1 068 855 A1.
English language DERWENT abstract of EP 1 068 856 A1.
English language DERWENT abstract of EP 1 086 945 A1.
English language DERWENT abstract of EP 1 090 627 B1.
English language DERWENT abstract of EP 1 114 636 A1.
English language DERWENT abstract of FR 2 232 303.
English language DERWENT abstract of FR 2 674 126.
English language DERWENT abstract of FR 2 785 179.
English language DERWENT abstract of FR 2 796 270.

English language DERWENT abstract of FR 2 796 271.
English language DERWENT abstract of FR 2 796 272.
English language DERWENT abstract of FR 2 796 273.
English language DERWENT abstract of FR 2 796 276.
English language DERWENT abstract of FR 2 802 806.
English language DERWENT abstract of FR 2 804 017.
English language DERWENT abstract of FR 2 804 018.
English language DERWENT abstract of FR 2 810 562.
English language DERWENT abstract of FR 2 811 225.
English language DERWENT abstract of FR 2 811 552.
English language DERWENT abstract of FR 2 816 506.
English language DERWENT abstract of FR 2 817 739.
English language DERWENT abstract of FR 2 817 740.
English language DERWENT abstract of FR 2 817 743.
English language DERWENT abstract of FR 2 819 399.
English language DERWENT abstract of FR 2 819 400.
English language DERWENT abstract of FR 2 819 402.
English language DERWENT abstract of JP 02/200612.
English language DERWENT abstract of JP 04/346909.
English language DERWENT abstract of JP 09/255560.
English language DERWENT abstract of JP 10/007527.
English language DERWENT abstract of JP 10/120903.
English language DERWENT abstract of JP 10/212213.
English language DERWENT abstract of JP 10/259344 A.
English language DERWENT abstract of JP 11/106216.
English language DERWENT abstract of JP 11/335228.
English language DERWENT abstract of JP 11/335242.
English language DERWENT abstract of JP 11/335254.
English language DERWENT abstract of JP 2000038314 A.
English language DERWENT abstract of JP 2000038316 A and JP 2000038317 A.
English language DERWENT abstract of JP 2000038321 A.
English language DERWENT abstract of JP 2000086427 A.
English language DERWENT abstract of JP 2000086429 A.
English language DERWENT abstract of JP 2000086438 A.
English language DERWENT abstract of JP 2127568.
English language DERWENT abstract of JP 2216279.
English language DERWENT abstract of JP 3014683.
English language abstract of JP 53043577 from Patent Abstracts of Japan.
English language abstract of JP 56123909 from Patent Abstracts of Japan.
English language abstract of JP 56166276 from Patent Abstracts of Japan.
English language abstract of JP 61065809 from Patent Abstracts of Japan.
English language DERWENT abstract of JP 7179795.
English language DERWENT abstract of JP 7267827.
English language DERWENT abstract of JP 8225316.
English language DERWENT abstract of JP 920631.
English language abstract of JP 9295922 A from Patent Abstracts of Japan.
English language DERWENT abstract of JP 62061911.
English language DERWENT abstract of WO 02/055031 A1.
English language DERWENT abstract of WO 02/056845 A1.
French Search Report in FR 0000920 (priority document for PCT/FR01/00229, dated Nov. 10, 2000.
French Search Report in FR 0001004, dated Nov. 10, 2000.
French Search Report in FR 0008084, dated Mar. 28, 2001.
French Search Report in FR 0008913, dated Mar. 20, 2001.
French Search Report in FR 0016161, dated Sep. 6, 2001.
French Search Report in FR 0016163, dated Aug. 1, 2001.
French Search Report in FR 0016164, dated Sep. 6, 2001.
French Search Report in FR 0016180, dated Oct. 16, 2001.
French Search Report in FR 0100479, dated Sep. 17, 2001.
French Search Report in FR 0100620, dated Nov. 6, 2001.
French Search Report in FR 0100623, dated Oct. 9, 2001.
French Search Report in FR 0114529, dated Aug. 26, 2002.
French Search Report in FR 0114530, dated Aug. 26, 2002.
French Search Report in FR 9909176, dated Mar. 23, 2000.
French Search Report in FR 9909177, dated Mar. 30, 2000.
French Search Report in FR 9916588, dated Oct. 16, 2000.
Handbook of Cosmetic Science and Tech. Elsevier Advanced Tech., 1st Edition (1994), p. 19.
International Search Report in PCT/FR01/00229, dated Apr. 18, 2001.
International Search Report in PCT/FR01/01958, dated Oct. 26, 2001.
International Search Report in PCT/FR01/03726, dated Apr. 18, 2002.
International Search Report in PCT/FR01/03937, dated Apr. 23, 2002.
International Search Report in PCT/FR01/03938, dated Jun. 10, 2002.
International Search Report in PCT/FR01/03939, dated Apr. 15, 2002.
International Search Report in PCT/FR01/03940, dated Mar. 13, 2002.
International Search Report in PCT/FR01/03945, dated May 31, 2002.
International Search Report in PCT/FR02/00129, dated Jun. 14, 2002.
International Search Report in PCT/FR02/00144, dated Jun. 14, 2002.
International Search Report in PCT/FR02/00194, dated Jun. 12, 2002.
International Search Report in PCT/IB00/02000, dated Aug. 8, 2001.
International Search Report in PCT/IB00/02002, dated Sep. 4, 2001.
International Search Report in PCT/IB00/02006, dated Aug. 8, 2001.
International Search Report in PCT/IB01/02780, dated Apr. 10, 2002.
International Search Report in PCT/IB01/02786, dated Oct. 2, 2002.
International Search Report in PCT/IB01/02820, dated May 27, 2002.
International Search Report in PCT/IB01/02833, dated May 24, 2002.
International Search Report in PCT/IB01/02840, dated Jun. 11, 2002.
International Search Report in PCT/US 00/33596, dated Aug. 8, 2001.
International Search Report in PCT/US 01/47454, dated Aug. 29, 2002.
International Search Report in PCT/US 01/47459, dated Feb. 6, 2003.
International Search Report in PCT/US 01/47496, dated Feb. 26, 2003.
International Search Report in PCT/US 01/47497, dated Sep. 10, 2002.
International Search Report in PCT/US 01/47499, dated Aug. 8, 2002.

Kenji Hanabusa et al., Easy Preparation and Prominent Gelation of New Gelator Based on L–Lysine, 2000 Chem. Letters, 1070–1071.

Kenji Hanabusa et al., Prominent Gelation and Chiral Aggregation of Alkylamides Derived from trans–1,2–Diaminocyclohexane, Angew. Chem. Int. Ed. Engl. 1996, 35, No. 17, 1949–1951.

Kenji Hanabusa et al., Terephthaloyl Derivatives as New Gelators; Excellent Gelation Ability and Remarkable Increase of Gel Strength by Adding Polymers, 1999 Chemistry Letters 767–768.

Kirk–Othmer, "Encyclopedia of Chemical Technology", Third Edition, vol. 22, John Wiley & Sons, 1983, pp. 332–342.

Milan Jokic et al., A Novel Type of Small Organic Gelators: Bis(Amino Acid) Oxalyl Amides, 1995 J. Chem. Soc., Chem. Commun., 1723–1724.

P. Terech, "Low–molecular Weight Organogelators," in Specialist Surfactants, ch. 8, pp. 208–268 (I.D. Robb, ed., 1997).

Partial International Search Report in PCT/US 01/47497, dated Aug. 30, 2002.

Toshimi Shimizu et al., Stereochemical Effect of Even–Odd Connecting Links on Supramolecular Assemblies Made of 1–Glucosamide Bolaamphiphiles, J. Am Chem. Soc. 1997, 119, 2812–2818.

Xuzhong Luo et al., Self–assembled organogels formed by monoalkyl derivatives of oxamide, 2000 Chem. Commun. 2091–92.

Yasuda et al., Novel Low–molecular–weight Organic Gels: "N,N',N–Tristearyltrimesamide/Organic Solvent System," Chemistry Letters, pp. 575–576, 1996, the month of publication is not available.

Charles M. Hansen, "The Three Dimensional Solubility Parameter—Key to Paint Component Affinities: I. Solvents, Plasticizers, Polymers, and Resins," Journal of Paint Technology, vol. 39, No. 505, Feb. 1967, pp. 104–117.

Co–Pending U.S. Appl. No. 09/618,032; issued as U.S. Appl. No. 6,402,408 on Jun. 11, 2002, Title: Composition Containing a Liquid Fatty Phase Gelled with a Polyamide Containing Ester End Groups filed Jul. 17, 2000.

Co–Pending U.S. Appl. No. 09/618,066; Title: Compositions in Rigid Form Structured with a Polymer filed Jul. 17, 2000.

Co–Pending U.S. Appl. No. 09/685,577; Title: Compositions in Rigid Form Structured with a Polymer filed Oct. 11, 2000.

Co–Pending U.S. Appl. No. 09/685,578; Title: Composition Containing a Liquid Fatty Phase Gelled with a Polyamide Containing Ester End Groups filed Oct. 11, 2000.

Co–Pending U.S. Appl. No. 09/733,896; Title: Compositions Containing Heteropolymers and Oil–Soluble Polymers and Methods of Using Same filed Dec. 12, 2000.

Co–Pending U.S. Appl. No. 09/733,897; Title: Compositions Containing Heteropolymers and Methods of Using Same filed Dec. 12, 2000.

Co–Pending U.S. Appl. No. 09/733,898; Title: Compositions Containing Heteropolymers and Oil–Soluble Esters and Methods of Using Same filed Dec. 12, 2000.

Co–Pending U.S. Appl. No. 09/733,899; Title: Cosmetic Compositions Containing at Least One Hetero Polymer and at Least One Film–Forming Silicone Resin and Methods of Using filed Dec. 12, 2000.

Co–Pending U.S. Appl. No. 09/733,900; Title: Cosmetic Compositions Containing Heteropolymers and Oil–Soluble Cationic Surfactants and Methods of Using filed Dec. 12, 2000.

Co–Pending U.S. Appl. No. 09/749,036; Title: Composition Comprising at Least One Hetero Polymer and at Least One Pasty Fatty Substance and Methods for Use filed Dec. 28, 2000.

Co–Pending U.S. Appl. No. 09/899,909, issued as U.S. Appl. No. 6,432,391 on Aug. 13, 2002, Title: Transparent Scented Solid Cosmetic Composition filed Jul. 9, 2001.

Co–Pending U.S. Appl. No. 09/937,314; Title: Transfer–Free Composition Structured in the Stiff Form by a Polymer filed Sep. 24, 2001.

Co–Pending U.S. Appl. No. 09/971,028, issued as U.S. Appl. No. 6,716,420 on Apr. 6, 2004; Title: Methods of Dispersing at Least One Coloring Agent Using at Least One Heteropolymer filed Oct. 5, 2001.

Co–Pending U.S. Appl. No. 10/012,029; Title: Cosmetic Composition Comprising a Polymer Blend filed Dec. 11, 2001.

Co–Pending U.S. Appl. No. 10/012,051; Title: Use of a Polymer for Obtaining an Express Make–Up of Keratin materials filed Dec. 11, 2001.

Co–Pending U.S. Appl. No. 10/012,052; Title: Cosmetic Composition Comprising a Wax and a Polymer filed Dec. 11, 2001.

Co–Pending U.S. Appl. No. 10/046,568; Title: Nail Polish Composition Comprising a Polymer filed Jan. 16, 2002.

Co–Pending U.S. Appl. No. 10/129,377; Title: Compositions Structured with a Polymer Containing a Heteroatom and an Organogelator filed May 3, 2002.

Co–Pending U.S. Appl. No. 10/182,830; Title: Cosmetic Composition Comprising Hetero Polymers and a Solid Substance and Method of Using Same Aug. 2, 2002.

Co–Pending U.S. Appl. No. 10/198,931, Title: Compositions Comprising at Least One Heteropolymer and Fibers, and Methods of Using the Same filed Jul. 22, 2002.

Co–Pending U.S. Appl. No. 10/203,018; Title: Composition Comprising at Least One Hetero Polymer and at Least One Inert Filler and Methods for Use filed Aug. 5, 2002.

Co–Pending U.S. Appl. No. 10/203,254; Title: Cosmetic Compositions Containing at Least One Heteropolymer and at Least One Gelling Agent and Methods of Using the Same Aug. 7, 2002.

Co–Pending U.S. Appl. No. 10/203,374, Title: Method for Making a Coloured Make–Up Cosmetic Composition with Controlled Transmittance filed Aug. 9, 2002.

Co–Pending U.S. Appl. No. 10/203,375, Title: Transparent or Translucent Colored Cosmetic Composition filed Aug. 9, 2002.

Co–Pending U.S. Appl. No. 10/312,083, Title: Solid Emulsion Containing a Liquid Fatty Phase Structured with a Polymer filed Dec. 23, 2002.

Co–Pending U.S. Appl. No. 10/413,217, Title: Methods of Dispersing at Least One Coloring Agent Using at Least One Heteropolymer filed Apr. 15, 2003.

Co–Pending U.S. Appl. No. 10/450,108, Title: Cosmetic Composition Comprising a Polymer and Fibres filed Jun. 11, 2003.

Co–Pending U.S. Appl. No. 10/459,636, Title: Cosmetic Emulsions Containing at Least One Hetero Polymer and at Least One Sunscreen and Methods of Using the Same filed Jun. 12, 2003.

Co-Pending U.S. Appl. No. 10/466,166, Title: Cosmetic Composition Comprising a Mixture of Polymers filed Jul. 14, 2003.
Co-Pending U.S. Appl. No. 10/618,315, Title: Cosmetic Composition Comprising a Structuring Agent, Silicone Powder and Swelling Agent filed Jul. 11, 2003.
Co-Pending U.S. Appl. No. 10/746,612, Title: Cosmetic Compositions Comprising a Structuring Agent, Silicone Powder and Swelling Agent filed Dec. 22, 2003.
Co-Pending U.S. Appl. No. 10/747,412, Title: Cosmetic Emulsions Containing at Least One Hetero Polymer and at Least One Sunscreen and Methods of Using the Same filed Dec. 22, 2003.
Co-Pending U.S. Appl. No. 10/787,440, Title: Composition Comprising at Least One Hetero Polymer and at Least One Inert FIller and Methods for Use filed Feb. 27, 2004.
Co-Pending U.S. Appl. No. 10/787,441, Title: Cosmetic Composition Comprising Hetero Polymers and a Solid Substance and Method of Using Same filed Feb. 27, 2004.
Co-Pending U.S. Appl. No. 10/699,780, Title: Methods of Dispersing at Least One Coloring Agent Using at Least One Heteropolymer filed Nov. 4, 2003.
Co-Pending U.S. Appl. No. 10/918,579, Title: Compositions Containing Heteropolymers and Oilsoluble Esters and Methods of Using Same filed Aug. 16, 2004.
Co-Pending U.S. Appl. No. 10/990,475, Title: Use of a Polymer for Obtaining an Express Make-Up of Keratin Materials filed Nov. 18, 2004.
Co-Pending U.S. Appl. No. 10/933,430, Title: Cosmetic Composition Comprising a Polymer Blend filed Nov. 22, 2004.
Co-Pending U.S. Appl. No. 10/933,431, Title: A Transfer-Free Composition Structured in Rigid Form by a Polymer filed Nov. 22, 2004.
Co-Pending U.S. Application No. Not Yet Assigned, Title: Cosmetic Composition Comprising Two Different Hetero Polymers and Method of Using Same filed Dec. 23, 2004.
English Language abstract of JP 53/043577 from Patent Abstracts of Japan.
English Language abstract of JP 56/123909 from Patent Abstracts of Japan.
English Language abstract of JP 56/166276 from Patent Abstracts of Japan.
English language DERWENT abstract of JP 78/043577.
English language DERWENT abstract of JP 61/065809.
English language DERWENT abstract of JP 9/295922.
English language DERWENT abstract of WO 01/97773 A1.
English language DERWENT abstract of WO 02/056847 A1.
English language DERWENT abstract of WO 02/056848 A1.
English language DERWENT abstract of WO 02/47622 A2.
English language DERWENT abstract of WO 02/47629 A1.
English language DERWENT abstract of WO 02/47630 A1.
English language DERWENT abstract of WO 86/04916.
Estee Lauder MagnaScopic Maximum Volume mascara product packaging, believed to have first been sold in 2003.
Estee Lauder's Response to Plaintiff's First Set of Interrogatories (Nos. 1–6), dated Sep. 27, 2004, in the on–going litigation *L'Oreal S.A., et al. v. The Estee Lauder Companies Inc. et al.*, Civil Action No. 04–1660 (D.N.J.).
Office Action in co-pending U.S. Appl. No. 09/618,066 dated Jul. 15, 2002 (Ex. Sheikh).
Office Action in co-pending U.S. Appl. No. 09/618,066 dated Jul. 16, 2003 (Ex. Sheikh).
Office Action in co-pending U.S. Appl. No. 09/618,066 dated Nov. 19, 2003 (Ex. Sheikh).
Office Action in co-pending U.S. Appl. No. 09/685,577 dated Aug. 11, 2004 (Ex. Venkat).
Office Action in co-pending U.S. Appl. No. 09/685,577 dated Jul. 15, 2002 (Ex. Sheikh).
Office Action in co-pending U.S. Appl. No. 09/685,577 dated Jul. 16, 2003 (Ex. Sheikh).
Office Action in co-pending U.S. Appl. No. 09/685,577 dated Nov. 19, 2003 (Ex. Sheikh).
Office Action in co-pending U.S. Appl. No. 09/685,578 dated Aug. 11, 2004 (Ex. Pryor).
Office Action in co-pending U.S. Appl. No. 09/685,578 dated May 7, 2003 (Ex. Pryor).
Office Action in co-pending U.S. Appl. No. 09/685,578 dated Nov. 19, 2003 (Ex. Pryor).
Office Action in co-pending U.S. Appl. No. 09/733,896 dated Jan. 28, 2003 (Ex. Rajguru).
Office Action in co-pending U.S. Appl. No. 09/733,896 dated Jul. 19, 2002 (Ex. Rajguru).
Office Action in co-pending U.S. Appl. No. 09/733,896 dated Nov. 18, 2003 (Ex. Rajguru).
Office Action in co-pending U.S. Appl. No. 09/733,897 dated Apr. 15, 2002 (Ex. Berman).
Office Action in co-pending U.S. Appl. No. 09/733,897 dated Apr. 23, 2003 (Ex. Wells).
Office Action in co-pending U.S. Appl. No. 09/733,897 dated Aug. 29, 2002 (Ex. Berman).
Office Action in co-pending U.S. Appl. No. 09/733,897 dated May 6, 2004 (Ex. Yu).
Office Action in co-pending U.S. Appl. No. 09/733,898 dated Apr. 29, 2003 (Ex. Yoon).
Office Action in co-pending U.S. Appl. No. 09/733,898 dated Aug. 28, 2002 (Ex. Yoon).
Office Action in co-pending U.S. Appl. No. 09/733,898 dated Dec. 23, 2003 (Ex. Yoon).
Office Action in co-pending U.S. Appl. No. 09/733,899 dated Apr. 7, 2004 (Ex. Lamm).
Office Action in co-pending U.S. Appl. No. 09/733,899 dated Apr. 9, 2003 (Ex. Lamm).
Office Action in co-pending U.S. Appl. No. 09/733,899 dated Sep. 22, 2004 (Ex. Venkat).
Office Action in co-pending U.S. Appl. No. 09/733,900 dated Apr. 7, 2004 (Ex. Lamm).
Office Action in co-pending U.S. Appl. No. 09/733,900 dated Jul. 16, 2003 (Ex. Lamm).
Office Action in co-pending U.S. Appl. No. 09/733,900 dated Dec. 1, 2004 (Ex. Venkat).
Office Action in co-pending U.S. Appl. No. 09/749,036 dated Aug. 13, 2003 (Ex. Howard).
Office Action in co-pending U.S. Appl. No. 09/749,036 dated Jul. 16, 2002 (Ex. Howard).
Office Action in co-pending U.S. Appl. No. 09/749,036 dated May 5, 2004 (Ex. Howard).
Office Action in co-pending U.S. Appl. No. 09/899,909 dated Dec. 18, 2001 (Ex. Dodson).
Office Action in co-pending U.S. Appl. No. 09/937,314 dated May 19, 2004 (Ex. Venkat).
Office Action in co-pending U.S. Appl. No. 09/971,028 dated Aug. 11, 2003 (Ex. Wang).
Office Action in co-pending U.S. Appl. No. 09/971,028 dated Mar. 26, 203 (Ex. Wang).

Office Action in co-pending U.S. Appl. No. 10/012,029 dated Nov. 20, 2002 (Ex. Venkat).
Office Action in co-pending U.S. Appl. No. 10/012,029 dated Sep. 8, 2003 (Ex. Venkat).
Office Action in co-pending U.S. Appl. No. 10/012,051 datd Jan. 14, 2003 (Ex. Venkat).
Office Action in co-pending U.S. Appl. No. 10/012,051 dated May 14, 2004 (Ex. Venkat).
Office Action in co-pending U.S. Appl. No. 10/012,051 dated Oct. 3, 2003 (Ex. Venkat).
Office Action in co-pending U.S. Appl. No. 10/012,052 dated Nov. 6, 2003 (Ex. Wells).
Office Action in co-pending U.S. Appl. No. 10/012,052 dated Aug. 9, 2004 (Ex. Wells).
Office Action in co-pending U.S. Appl. No. 10/046,568 dated Dec. 30, 2003 (Ex. Venkat).
Office Action in co-pending U.S. Appl. No. 10/046,568 dated Jun. 12, 2003 (Ex. Venkat).
Office Action in co-pending U.S. Appl. No. 10/046,568 dated Nov. 5, 2002 (Ex. Venkat).
Office Action in co-pending U.S. Appl. No. 10/046,568 dated Sep. 22, 2004 (Ex. Venkat).
Office Action in co-pending U.S. Appl. No. 10/182,830 dated Aug. 24, 2004 (Ex. Venkat).
Office Action in co-pending U.S. Appl. No. 10/198,931 dated Dec. 18, 2003 (Ex. Venkat).
Office Action in co-pending U.S. Appl. No. 10/198,931 dated Sep. 1, 2004 (Ex. Venkat).
Office Action in co-pending U.S. Appl. No. 10/203,018 dated May 19, 2004 (Ex. Venkat).
Office Action in co-pending U.S. Appl. No. 10/312,083 dated Oct. 1, 2004 (Ex. Venkat).
Office Action in co-pending U.S. Appl. No. 10/413,217 dated Sep. 9, 2004 (Ex. Venkat).
Office Action in co-pending U.S. Appl. No. 10/699,780 dated Sep. 22, 2004 (Ex. Venkat).
Office Action in co-pending U.S. Appl. No. 10/746,612 dated Sep. 20, 2004 (Ex. Venkat).
Office Action in co-pending U.S. Appl. No. 10/787,440 dated Aug. 24, 2004 (Ex. Venkat).
Origins Full StoryTM Lush lash mascara product packaging, believed to have first been sold in 2003.
PCT Application No. PCT/FR01/03962; Title: Composition Comprising at Least One Heteropolymer and at Least One Inert Filler and Methods for USE filed Dec. 12, 2001.
PCT Application No. PCT/FR01/03963; Title: Cosmetic Compositions Containing at Least One Heteropolymer and at Least One Gelling Agent and Methods of Using the Same filed Dec. 12, 2001.
PCT Application No. PCT/FR01/03965; Title Cosmetic Composition Comprising Hetero Polymers and a Solid Substance and Method of Using Same filed Dec. 12, 2001.
PCT Application No. PCT/IB00/02000; Title: Composition Comprising at Least One Hetero Polymer and at Least One Inert Filler and Methods for Use filed date Dec. 12, 2000.
PCT Application No. PCT/IB00/02006; Title: Cosmetic Compositions Containing at Least One Heteropolymer and at Least One Gelling Agent and Methods of Using the Same filed Dec. 12, 2000.
PCT Application No. PCT/IB01/02780; Title:Composition Structured with a Polymer Containing a Heteroatom Organogelator International filed Dec. 12, 2001.
PCT Application No. PCT/US00/33596; Title Cosmetic Composition Comprising Hetero Polymers and a Solid Substance and Method of Using Same filed Dec. 12, 2000.
PCT Application No. PCT/US01/47454; Title: Composition Containing Heteropolymers and Oil-Soluble Polymers and Methods of Using Same filed Dec. 12, 2001.
PCT Application No. PCT/US01/47459; Title: Cosmetic Compositions Containing at Least One Hetero Polymer and at Least One Film-Forming Silicone Resin and Methods of Using filed Dec. 12, 2001.
PCT Application No. PCT/US01/47496; Title: Compositions Containing Heteropolymers and Methods of Using Same filed Dec. 12, 2001.
PCT Application No. PCT/US01/47497; Title: Compositions Containing Heteropolymers and Oil-Soluble Esters and Methods of Using Same filed Dec. 12, 2001.
PCT Application No. PCT/US01/47499; Title: Cosmetic Compositions Containing Heteropolymers and Oil-Soluble Cationic Surfactants and Methods of Using Same filed Dec. 12, 2001.
PCT Application No. PCT/US03/41618; Title: Cosmetic Compositions Comprising a Structuring Agent, Silicone Powder and Swelling Agent filed Dec. 22, 2003.
PCT Application No. PCT/US04/01071; Title: Long Wear Cosmetic Composition filed Jan. 16, 2004.
McCutcheon's vol. 1: Emuslifiers & Detergents, North American Edition, MC Publishing Co., Glen Rock NJ (1993), pp. 272–273.
U.S. District Court for the Distric of New Jersey Civel Docket for *L'Oreal S.A. v. Estee Lauder Companies, Inc.*, Civ. No. 04–1660 (HAA) (D.N.J. filed Apr. 4, 2004) (retrieved Jan. 2, 2005).

\* cited by examiner

COSMETIC COMPOSITION CONTAINING A POLYMER AND A FLUORO OIL

The present invention relates to a care composition and/or treatment composition and/or make-up composition for the skin, including the scalp, and/or the lips of humans, containing a liquid fatty phase containing a fluoro oil, structured with a particular polymer. This composition is especially in the form of a make-up stick and more especially a lipstick, which, when applied, gives a noteworthy shiny, non-sticky, transfer-resistant deposit.

It is common to find a structured, i.e. gelled and/or rigidified, liquid fatty phase in cosmetic or dermatological products; this is especially the case in solid compositions such as deodorants, lip balms, lipsticks, concealer products and cast foundations. This structuring is obtained with the aid of waxes and/or fillers. Unfortunately, these waxes and fillers have a tendency to make the composition matt, which is not always desirable, in particular for a lipstick; specifically, women are always looking for lipstick in the form of a tube depositing a film that is increasingly glossy.

For the purposes of the invention, the expression "liquid fatty phase" means a fatty phase that is liquid at room temperature (25° C.), composed of one or more fatty substances that are liquid at room temperature, also known as oils, that are generally mutually compatible.

The structuring of the liquid fatty phase makes it possible in particular to limit its exudation from solid compositions, in particular in hot and humid regions, and in addition to limit, after deposition on the skin or the lips, the migration of this phase into the wrinkles and fine lines, which is particularly desired for a lipstick. Specifically, significant migration of the liquid fatty phase, in particular when it is charged with dyestuffs, leads to an unaesthetic effect around the lips and the eyes, which particularly accentuates the wrinkles and fine lines. This migration is often mentioned by women as being a major defect of conventional lipsticks.

The gloss is essentially associated with the nature of the liquid fatty phase. Thus, it is possible to reduce the content of waxes and of fillers in the composition in order to increase the gloss of a lipstick, but in this case the migration of the liquid fatty phase increases. In other words, the content of waxes and of fillers required to prepare a stick of suitable hardness which does not exude at room temperature is a restricting factor on the gloss of the deposit.

The Applicant has found that the loss of gloss of a stick containing waxes is associated with the anisotropic crystal structure of these compounds. It has therefore envisaged manufacturing a stick while reducing the amount of waxes and/or fillers.

Furthermore, most make-up compositions or care compositions, when applied to the skin, the eyelashes or the lips, have the drawback of transferring, i.e. of becoming at least partly deposited, leaving marks, on certain supports with which they may come into contact, and especially a glass, a cup, a cigarette, an item of clothing or the skin. This results in mediocre persistence of the film applied, making it necessary to regularly reapply the composition, especially a foundation or lipstick. However, users nowadays wish to achieve a beauty enhancement of their face, including the lips, and their body while spending as little time as possible doing so. Moreover, the appearance of these unacceptable marks, especially on blouse collars, may put certain women off using this type of make-up.

Cosmeticians have been interested for many years in "transfer-resistant" lipstick compositions and more recently in transfer-resistant foundation compositions. Thus, the company Shiseido at envisaged, in its patent application JP-A-61-65809, transfer-resistant lipstick compositions containing a siloxysilicate resin (with a three-dimensional network), a volatile silicone oil containing a cyclic silicone chain and pulverulent fillers. Similarly, the company Noevier at disclosed, in document JP-A-62-61911, transfer-resistant lipstick, eyeliner and foundation compositions comprising one or more volatile silicones combined with one or more hydrocarbon-based waxes.

Although these compositions have improved transfer-resistance properties, they have the drawback of leaving on the lips, after the silicone oils have evaporated off, a film which becomes uncomfortable over time (sensation of drying out and of tautness), which puts a certain number of women off this type of lipstick. In addition, the film deposited is matt.

Patent application EP-A-0 749 746 from L'Oréal discloses lipstick compositions containing a dispersion of polymer particles that are surface-stabilized with a polymer stabilizer. These compositions have the drawback of containing only a small proportion of polar oils that are known to give sheen to the film deposited, in conventional compositions. In particular, the presence of a large proportion of polar oils (at least 5%) results in flocculation of the particles and thus instability over time of the compositions.

A need thus remains for a composition which does not have the above drawbacks, and which especially has noteworthy transfer-resistance properties, even in the case of a pronounced pressure or friction, good staying power over time, a glossy appearance, and which is not sticky and does not dry out the skin or the lips onto which it is applied, either during application or over time. Furthermore, this composition is stable over time and easy to manufacture, and it is easy to introduce pigments therein.

A subject of the invention is, precisely, a care composition and/or make-up composition and/or treatment composition for the skin and/or the lips of the face and/or for integuments, which overcomes the drawbacks mentioned above.

Surprisingly, the Applicant has found that the use of particular polymers combined with a fluoro oil makes it possible to obtain a stick which, when applied to the lips, gives a film with noteworthy cosmetic properties. In particular, the film is glossy, flexible, comfortable, "transfer-resistant" and non-sticky. In addition, the film shows good homogeneity. Furthermore, the composition is stable over time and does not exude at room temperature.

Moreover, when the fluoro oil is a silicone fluoro oil, the said oil is highly compatible with non-fluoro silicone oils: it is then possible to incorporate a larger amount of silicone oil into the composition, which further promotes the staying power of the lipstick.

The term "stable" means a composition that does not exude at room temperature for at least 2 minus, or even up to 9 months.

The invention applies not only to make-up products for the lips, such as lipsticks, lip glosses and lip pencils, but also to care and/or treatment products for the skin, including the scalp, and for the lips, such as antisun products especially in stick form for the skin of the face, the body or the lips, make-up products for the skin, both of the human face and of the human body, such as foundations optionally cast in stick or dish form, concealer products, eye shadows, and transfer tattoos, body hygiene products such as deodorants, especially in stick form, shampoos, conditioners and make-up products for the eyes such as eyeliners, eye pencils and mascaras, more especially in cake form, as well as care products for the face, the body and keratin fibres such as the hair and the eyebrows.

More specifically, a subject of the invention is a structured composition containing at least one liquid fatty phase comprising at least one fluoro oil, the liquid fatty phase being structured with at least one polymer with a weight-average molecular mass of less than or equal to 100 000, comprising a) a polymer skeleton having hydrocarbon-based repeating units containing at least one hetero atom, and b) optionally pendent and/or terminal fatty chains that are optionally functionalized, containing from 6 to 120 carbon atoms and being linked to these hydrocarbon-based units, the liquid fatty phase and the polymer forming a physiologically acceptable medium.

The composition of the invention advantageously contains no silicone resin containing siloxysilicate or trimethylated silica units, so as to preserve the comfort properties of the composition.

The composition of the invention can be in the form of a paste, a solid or a more or less viscous cream. It can be an oil-in-water or water-in-oil emulsion, or a rigid or soft anhydrous gel. In particular, it is in a form cast as a stick or a dish and more especially in the form of an anhydrous rigid gel, especially an anhydrous stick. More especially, it is in the form of a rigid gel that is translucent or transparent, the liquid fatty phase forming the continuous phase.

The gelling of the oil can be modified according to the nature of the hetero atom-containing polymer used, and may be such that a rigid structure in the form of a tube or a stick is obtained. When these tubes are coloured, they make it possible, after application, to obtain a glossy deposit of uniform colour, that does not transfer, in particular onto a support placed in contact with the film, after evaporation of the volatile solvent, and that has good staying power, especially of the colour over time.

The structuring polymer of the composition of the invention is a solid that is undeformable at room temperature (25° C.). It is capable of structuring the composition without opacifying it.

For the purposes of the invention, the expression "functionalized chains" means an alkyl chain comprising one or more functional or reactive groups chosen in particular from amide, hydroxyl, ether, oxyalkylene, polyoxyalkylene, halogen, including fluoro or perfluoro, ester, siloxane and polysiloxane groups. In addition, the hydrogen atoms of one or more fatty chains may be substituted at least partially with fluorine atoms.

According to the invention, these chains may be linked directly to the polymer skeleton or via an ester function or a perfluoro group.

For the purposes of the invention, the term "polymer" means a compound containing at least 2 repeating units and preferably at least 3 repeating units, which are identical.

For the purposes of the invention, the expression "hydrocarbon-based repeating units" means a unit containing from 2 to 80 carbon atoms and preferably from 2 to 60 carbon atoms, bearing hydrogen atoms and optionally oxygen atoms, which may be linear, branched or cyclic, and saturated or unsaturated. These units each also comprise one or more hetero atoms that are advantageously non-pendent and are in the polymer skeleton. These hetero atoms are chosen from nitrogen, sulphur and phosphorus atoms and combinations thereof, optionally combined with one or more oxygen atoms. Preferably, the units comprise at least one nitrogen atom, in particular a non-pendent nitrogen atom. These units also advantageously comprise a carbonyl group.

The units containing a hetero atom are, in particular, amide units forming a skeleton of the polyamide type, carbamate and/or urea units forming a polyurethane, polyurea and/or polyurea-urethane skeleton. These units are preferably amide units. The pendent chains are advantageously linked directly to at least one of the hetero atoms of the polymer skeleton. According to one embodiment, the first polymer comprises a polyamide skeleton.

Between the hydrocarbon-based units, the polymer may comprise silicone units or oxyalkylene units.

In addition, the polymer in the composition of the invention advantageously comprises a total number of fatty chains which represents from 40% to 98% of the total number of units containing a hetero atom and of fatty chains, and better still from 50% to 95%. The nature and proportion of the units containing a hetero atom depends on the nature of the organic phase and is, in particular, similar to the polar nature of the organic phase. Thus, the more the units containing a hetero atom are polar and in high proportion in the first polymer, which corresponds to the presence of several hetero atoms, the greater the affinity of the first polymer for polar oils. Conversely, the more the units containing a hetero atom are non-polar, or even apolar, or the lower the proportion thereof, the greater the affinity of the first polymer for apolar oils.

A subject of the invention is also a structured composition containing at least one liquid fatty phase comprising at least one fluoro oil, the liquid fatty phase being structured with at least one polyamide with a weight-average molecular mass of less than 100 000, comprising a) a polymer skeleton containing amide repeating units and b) optionally pendent and/or terminal fatty chains that are optionally functionalized, containing from 6 to 120 carbon atoms and being linked to these amide units, the liquid fatty phase and the polymer forming a physiologically acceptable medium.

The pendent fatty chains are preferably linked to at least one of the nitrogen atoms in the amide units of the polymer.

In particular, the fatty chains of this polyamide represent from 40% to 98% relative to the total number of amide units and of fatty chains, and better still from 50% to 95%.

Advantageously, the polymer and in particular the polyamide in the composition according to the invention has a weight-average molecular mass of less than or equal to 100 000 (in particular ranging from 1 000 to 100 000), in particular less than or equal to 50 000 (especially ranging from 1 000 to 50 000), more particularly ranging from 1 000 to 30 000, preferably from 2 000 to 20 000 and better still from 2 000 to 10 000.

As preferred structuring polymers which may be used in the invention, mention may be made of polyamides branched with pendent fatty chains and/or terminal fatty chains having from 12 to 120 carbon atoms and especially from 12 to 68 carbon atoms, the terminal fatty chains being linked to the polyamide skeleton via ester groups. These polymers are more especially those disclosed in document U.S. Pat. No. 5,783,657 from the company Union Camp. Each of these polymers in particular satisfies formula (I) below:

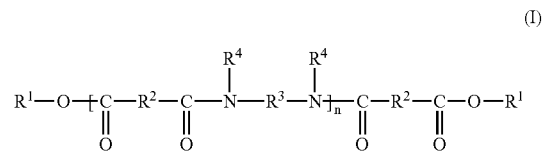

(I)

in which n denotes a number of amide units such that the number of ester groups represents from 10% to 50% of the total number of ester and amide groups; $R^1$ is, independently in each case, an alkyl or alkenyl group containing at least 4 carbon atoms; $R^2$ represents, independently in each case, a $C_4$ to $C_{42}$ hydrocarbon-based group, on condition that 50% of the groups $R^2$ represent a $C_{30}$ to $C_{42}$ hydrocarbon-based group; $R^3$ represents, independently in each case, an organic group containing at least 2 carbon atoms, hydrogen atoms and optionally one or more oxygen or nitrogen atoms; and $R^4$ represents, independently in each case, a hydrogen atom, a $C_1$ to $C_{10}$ alkyl group or a direct bond to $R^3$ or to another $R^4$, such that the nitrogen atom to which $R^3$ and $R^4$ are both attached forms part of a heterocyclic structure defined by $R^4$—N—$R^3$, with at least 50% of the groups $R^4$ representing a hydrogen atom.

In particular, the ester groups of formula (I), which form part of the terminal and/or pendent fatty chains for the purposes of the invention, represent from 15% to 40% of the total number of ester and amide groups and better still from 20% to 35%. Furthermore, n is advantageously an integer ranging from 1 to 5. Preferably, $R^1$ is a $C_{12}$ to $C_{22}$ and preferably $C_{16}$ to $C_{22}$ alkyl group. Advantageously, $R^2$ can be a $C_{10}$ to $C_{42}$ hydrocarbon-based (especially alkyl or alkenyl) group having the structure of a polymerized fatty acid or of a dimer from which the carboxylic acid groups have been removed (these groups serving for the formation of an amide). Preferably, at least 50% and better still at least 75% of the groups $R^2$ are groups containing from 30 to 42 carbon atoms. The other groups $R^2$ are $C_4$ to $C_{19}$ and better still $C_4$ to $C_{12}$ hydrogen-containing groups. Preferably, $R^3$ represents a $C_2$ to $C_{36}$ hydrocarbon-based group or a polyoxyalkylene group and $R^4$ represents a hydrogen atom. Preferably, $R^3$ represents a $C_2$ to $C_{12}$ hydrocarbon-based group. The hydrocarbon-based groups may be linear, cyclic or branched, and saturated or unsaturated groups. Moreover, the alkyl and alkenyl groups may be linear or branched groups.

According to the invention, the structuring of the liquid fatty phase is obtained with the aid of one or more polymers of formula (I). In general, the polymers of formula (I) are in the form of mixtures of polymers, these mixtures also possibly containing a synthetic product such as n is 0, i.e. a diester.

As examples of structuring polymers which can be used in the composition according to the invention, mention may be made of the commercial products sold by the company Bush Boake Allen under the names Uniclear 80 and Uniclear 100. They are sold, respectively, in the form of an 80% (in terms of active aterial) gel in a mineral oil and a 100% (in terms of active material) gel. They have a softening point of from 88 to 94° C. These commercial products are a mixture of a copolymer of a $C_{36}$ diacid coupled with ethylenediamine, having an average molecular mass of about 6 000. The remaining acid endings are, moreover, esterified with cetylstearyl alcohol).

As structuring polymers which can be used in the invention, mention may also be made of polyamide resins resulting from the condensation of an aliphatic dicarboxylic acid and a diamine (including compounds containing more than 2 carbonyl groups and 2 amine groups), the carbonyl and amine groups of adjacent individual units being condensed via an amide bond. These polyamide resins are, in particular, those sold under the brand name Versamid® by the companies General Mills Inc. and Henkel Corp. (Versamid 930, 744 or 1655) or by the company Olin Mathieson Chemical Corp. under the brand name Onamid®, in particular Onamid S or C. These resins have a weight-average molecular mass ranging from 6 000 to 9 000. For further information regarding these polyamides, reference may be made to the documents U.S. Pat. No. 3,645,705 and U.S. Pat. No. 3,148,125. More especially, Versamid® 930 or 744 is used.

The polyamides sold by the company Union Camp Corp. under the references Uni-Rez® (2658, 2931, 2970, 2621, 2613, 2624, 2665, 1554, 2623 and 2662) and the product sold under the reference Macromelt 6212 by the company Henkel may also useful. For further information regarding these polyamides, reference may be made to document U.S. Pat. No. 5,500,209.

It is also possible to use polyamide resins derived from plants, such as those described in U.S. Pat. No. 5,783,657 and U.S. Pat. No. 5,998,570, the content of which is incorporated into the present patent application by way of reference.

The structuring polymers in the composition of the invention advantageously have a softening point of greater than 70° C., and which may be up to 190° C. It preferably has a softening point ranging from 80 to 130° C. These polymers are, in particular, non-waxy polymers.

The term "fluoro oil" means any liquid fatty substance containing at least one fluorine atom. The fluoro oil may especially be a volatile fluoro oil. It preferably has a density of greater than about 1, for example greater than about 1.1, especially greater than about 1.2. It may have a saturating vapour pressure, at 25° C., at least equal to 50 Pa, for example greater than 2 000 Pa and preferably greater than 4 000 Pa.

The fluoro oil may advantageously have a boiling point (at ambient pressure, i.e. 760 mmHg or $10^5$ Pa) of between 20 and 75° C. and preferably between 25 and 65° C.

Fluoro oils which may be used in the invention include:

i) fluorosilicone compounds of formula (II):

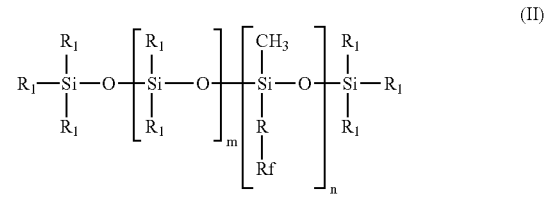

in which:

R represents a linear or branched divalent alkyl group containing 1 to 6 carbon atoms, preferably a divalent methyl, ethyl, propyl or butyl group, Rf represents a fluoroalkyl radical, especially a perfluoroalkyl radical, containing 1 to 9 carbon atoms, preferably 1 to 4 carbon atoms, $R_1$ represents, independently of each other, a C1–C20 alkyl radical, a hydroxyl radical or a phenyl radical, m is chosen from 0 to 150 and preferably from 20 to 100, and n is chosen from 1 to 300 and preferably from 1 to 100.

Preferably, the groups $R_1$ are identical and represent a methyl radical.

In one particularly preferred embodiment, the fluorosilicone compound used according to the invention is of formula (III) below:

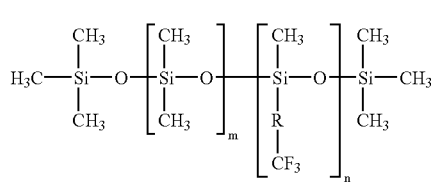
(III)

with

R representing a divalent methyl, ethyl, propyl or butyl group,
m being chosen from 0 to 80, and
n being chosen from 1 to 30.

Such compounds are, especially, those sold by the company Shin Etsu under the names 'X22-819', 'X22-820', 'X22-821', and 'X22-822' or 'FL-100'.

ii) the perfluorocycloalkyl compounds of formula (IV) below:

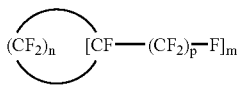
(IV)

in which n is equal to 4 or 5, m is equal to 1 or 2, and p is equal to 1, 2 or 3;
with the proviso that when g=2, the groups are not necessarily alpha to each other.

Among the compounds of formula (IV) that may especially be mentioned are perfluoromethylcyclopentane and perfluorodimethylcyclohexane, sold, respectively, under the names "Flutec PC1®" with a vapour pressure of 368 mbar, and "Flutec PC3®" by the company BNFL Fluorochemicals Ltd, and also perfluorodimethyl-cyclobutane.

iii) the fluoroalkyl or heterofluoroalkyl compounds corresponding to formula (V) below:

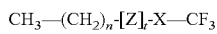
$CH_3—(CH_2)_n-[Z]_t-X—CF_3$ (V)

in which t is 0 or 1; n is 0, 1, 2 or 3; X is a linear or branched divalent perfluoroalkyl radical containing from 2 to 5 carbon atoms, and Z represents O, S or NR, R being hydrogen, a radical $—(CH_2)_n—CH_3$ or $—(CF_2)_m—CF_3$, m being 2, 3, 4 or 5.

Among the fluoroalkyl or heterofluoroalkyl compounds of formula (V) that may especially be mentioned are methoxynonafluorobutane sold under the name "MSX 4518®", "HFE-7100®" by the company 3M and ethoxynonafluorobutane sold under the name "HFE-7200®" by the company 3M.

iv) the perfluoroalkane compounds corresponding to formula (VI) below:

$CF_3—(CF_2)_n—CF_3$ (VI)

in which n is 2 to 6.

Among the perfluoroalkane compounds of formula (VI) that may especially be mentioned are dodecafluoropentane and tetradecafluorohexane.

v) the perfluoromorpholine derivatives corresponding to formula (VII) below:

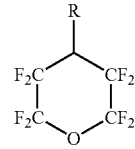
(VII)

in which R represents a $C_1$–$C_4$ perfluoroalkyl radical.

Among the perfluoromorpholine derivatives of formula (VII) that may especially be mentioned are 4-trifluoromethylperfluoromorpholine and 4-pentafluoroethylperfluoromorpholine.

(vi) the perfluoropolyethers corresponding to formulae (VIII) and (IX) below:

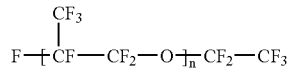
(VIII)

in which n is 7 to 30; and

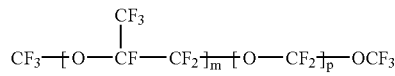
(IX)

the ratio m/p being from 20 to 40, and the molecular weight ranging from 500 to 20 000.

Among these perfluoropolyethers of formulae (VIII) and (IX), mention may be made, respectively, of the product sold under the name "Fluortress LM36®" by the company DuPont, and those sold under the general name "Fomblin" by the company Montefluos, for example Fomblin HC R®.

It is also possible to use the perfluoropolyethers mentioned in patent application EP-A-641 194, the content of which is incorporated into the present patent application by way of reference.

vii) the fluorosilicone compounds corresponding to formula (X) below:

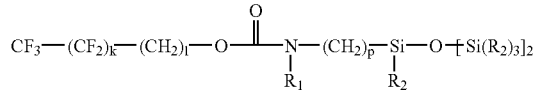
(X)

in which k is 1 to 17, l is 1 to 18, p is 1 to 6 and $R_1$ represents a hydrogen atom or a $C_1$–$C_6$ alkyl radical; $R_2$ represents a $C_1$–$C_6$ alkyl radical or a radical $—OSi(R_3)_3$, and $R_3$ represents a $C_1$–$C_4$ alkyl radical.

Among the compounds corresponding to formula (IV), mention may especially be made of:
N-(2-F-octylethyloxycarbonyl)-3-aminopropylbis(trimethylsiloxy)methylsilane,
N-(2-F-hexylethyloxycarbonyl)-3-aminopropylbis(trimethylsiloxy)methylsilane,
N-(2-F-butylethyloxycarbonyl)-3-aminopropylbis(trimethylsiloxy)methylsilane,
N-(2-F-octylethyloxycarbonyl)-3-aminopropyltris(trimethylsiloxy)silane,
N-(2-F-hexylethyloxycarbonyl)-3-aminopropyltris(trimethylsiloxy)silane, and N-(2-F-butylethyloxycarbonyl)-3-aminopropyltris(trimethylsiloxy)silane.
viii) the fluoroalkylsilicones corresponding to one of the formulae (XI) and/or (XII) below:

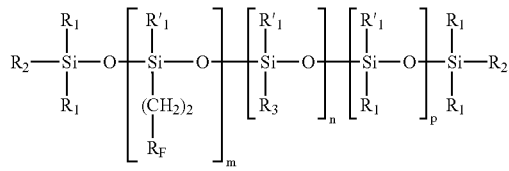

(XI)

in which $R_1$ and $R'_1$ independently represent a linear or branched alkyl radical containing from 1 to 6 carbon atoms, or a phenyl radical,
$R_2$ represents $R_1$, —OH or —$(CH_2)_f$—$R_F$, f being an integer ranging from 0 to 10,
$R_3$ represents a linear or branched alkyl radical containing from 6 to 22 carbon atoms,
$R_F$ represents a radical of formula —$(CF_2)_q$—$CF_3$, q being an integer ranging from 0 to 10,
m and n represent an integer ranging from 1 to 50, and
p represents an integer ranging from 0 to 2 000,

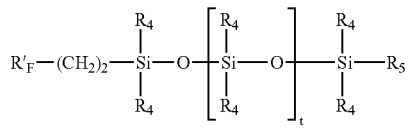

(XII)

in which:
$R_4$ represents a linear or branched alkyl radical containing from 1 to 6 carbon atoms, or a phenyl radical,
$R_5$ represents a linear or branched alkyl radical containing from 6 to 22 carbon atoms, or a phenyl radical,
$R'_F$ represents a radical of formula —$(CF_2)_s$—$CF_3$, s being an integer ranging from 0 to 15, and
t represents an integer ranging from 1 to 2 000.

According to one particular embodiment of the cosmetic compositions according to the invention, the fluoroalkylsilicone corresponds to formula (XI) in which:
$R_1$, $R'_1$ and $R_2$ represent a methyl radical,
$R_3$ represents a linear alkyl radical containing from 6 to 22 carbon atoms,
m and n are integers ranging from 1 to 20, and
q is an integer ranging from 1 to 13.

According to another embodiment of the compositions according to the invention, the fluoroalkylsilicone corresponds to formula (XII) in which:
$R_4$ represents a methyl radical,
$R_5$ represents a linear alkyl radical containing from 6 to 22 carbon atoms, and
s represents an integer ranging from 1 to 13.

The fluoroalkylsilicones as defined above are known compounds which have been described especially in U.S. Pat. No. 5,473,038.

Fluoro oils which may also be used are the fluorohydrocarbons mentioned in patent application EP-A-609 132, the content of which is incorporated into the present patent application by way of reference.

The fluoro oil may be present in the composition according to the invention in a content ranging from 0.1% to 50% by weight, relative to the total weight of the composition, preferably ranging from 1% to 30% by weight and better still ranging from 3% to 15% by weight.

Advantageously, the polymer may be combined with at least one amphiphilic compound that is liquid and non-volatile at room temperature, with a hydrophilic/lipophilic balance (HLB) value of less than 12 and especially ranging from 1 to 8 and preferably from 1 to 5. According to the invention, one or more amphiphilic compounds may be used. The aim of these amphiphilic compounds is to reinforce the structuring properties of the polymer containing a hetero atom, to make the polymer easier to use and to improve the ability of the stick to be deposited.

According to the invention, the composition can have a hardness ranging from 20 to 2 000 g, in particular from 20 to 1 500 g and better still from 20 to 900 g, for example from 50 to 600 g or better still from 150 to 450 g. This hardness may be measured according to a method of penetration of a probe into the said composition and in particular using a texture analyser (for example TA-XT2i from Rhéo) equipped with an ebonite cylinder 5 mm high and 8 mm in diameter. The hardness measurement is carried out at 20° C. at the centre of 5 samples of the said composition. The cylinder is introduced into each composition sample at a pre-speed of 2 mm/s, then at a speed of 0.5 mm/s and finally at a post-speed of 2 mm/s, the total displacement being 1 mm. The hardness value taken is that of the maximum peak. The measurement error is +/−50 g.

The hardness can also be measured by the "cheese wire" method, which consists in cutting a tube of lipstick 8.1 mm in diameter and in measuring the hardness at 20° C. using a DFGHS 2 tensile testing machine from the company Indelco-Chatillon, travelling at a speed of 100 mm/minute. It is expressed as the shear force (expressed in grams) required to cut a stick under these conditions. According to this method, the hardness of a composition in stick form according to the invention ranges from 30 to 300 g, better still from 30 to 250 g, especially from 30 to 150 g, preferably from 30 to 120 g, and for example from 30 to 50 g.

The hardness of the composition according to the invention is such that the composition is self-supporting and can disintegrate easily to form a satisfactory deposit on the skin and/or the lips and/or the integuments. In addition, with this hardness, the composition of the invention has good impact strength.

According to the invention, the composition in stick form has the behaviour of a deformable, flexible elastic solid, giving noteworthy elastic softness on application. The compositions in stick form of the prior art do not have this property of elasticity and flexibility.

The amphiphilic compound(s) which can be used in the composition of the invention comprise a lipophilic part linked to a polar part, the lipophilic part comprising a carbon-based chain containing at least 8 carbon atoms, in particular from 18 to 32 carbon atoms and better still from 18 to 28 carbon atoms. The polar part of this or these amphiphilic compound(s) is preferably the residue of a compound chosen from alcohols and polyols containing from 1 to 12 hydroxyl groups, and polyoxyalkylenes comprising at least 2 oxyalkylene units and containing from 0 to 20 oxypropylene units and/or from 0 to 20 oxyethylene units. In particular, the amphiphilic compound is an ester chosen from the hydroxystearates, oleates and isostearates of glycerol, of sorbitan or of methylglucose, or alternatively branched $C_{12}$ to $C_{26}$ fatty alcohols such as octyldodecanol, and mixtures thereof. Among these esters, monoesters and mixtures of mono- and diesters are preferred.

The content of amphiphilic compound and that of the polymer containing a hetero atom are chosen according to the desired gel hardness and as a function of the specific application envisaged. The respective amounts of polymer and of amphiphilic compound should be such that they produce a stick which can be worn down. In practice, the amount of polymer represents from 0.5 to 80% of the total weight of the composition, and better still from 5% to 40%. The amount of amphiphilic compound in practice represents from 0.1% to 35% of the total weight of the composition and better still from 1% to 15%, if it is present.

The liquid fatty phase in the composition according to the invention may comprise an additional oil, other than the fluoro oil described above (the additional oil is thus a non-fluoro oil). In particular, the additional oil may be a volatile oil or a non-volatile oil.

The liquid fatty phase of the composition advantageously contains more than 40% of liquid oil(s) containing a group similar to that of the units containing a hetero atom, and better still from 50% to 100%. In particular, the liquid fatty phase structured with a polyamide-type skeleton contains a high quantity, i.e. greater than 40% of the total weight of the liquid fatty phase and better still from 50% to 100%, of liquid apolar and more especially hydrocarbon-based oil or mixture of oils.

For a liquid fatty phase structured with a polymer containing a partially silicone-based skeleton, this fatty phase preferably contains more than 40% of the total weight of the liquid fatty phase and better still from 50% to 100%, of silicone-based liquid oil or mixture of oils, relative to the total weight of the liquid fatty phase.

For a liquid fatty phase structured with an apolar polymer of the hydrocarbon-based type, this fatty phase advantageously contains more than 40% by weight and better still from 50% to 100%, of liquid apolar and in particular hydrocarbon-based oil or mixture of oils, relative to the total weight of the liquid fatty phase.

In particular, the polar oils of the invention are:
hydrocarbon-based plant oils with a high content of triglycerides consisting of fatty acid esters of glycerol in which the fatty acids may have varied chain lengths from $C_4$ to $C_{24}$, these chains possibly being linear or branched, and saturated or unsaturated; these oils are, in particular, wheat germ oil, corn oil, sunflower oil, karite butter, castor oil, sweet almond oil, macadamia oil, apricot oil, soybean oil, cotton oil, alfalfa oil, poppy oil, pumpkin oil, sesame oil, marrow oil, rapeseed oil, avocado oil, hazelnut oil, grapeseed oil, blackcurrant seed oil, evening primrose oil, millet oil, barley oil, quinoa oil, olive oil, rye oil, safflower oil, candlenut oil, passionflower oil and musk rose oil; or alternatively caprylic/capric acid triglycerides such as those sold by the company Stearineries Dubois or those sold under the names Miglyol 810, 812 and 818 by the company Dynamit Nobel;
synthetic oils or synthetic esters of formula $R_5COOR_6$ in which $R_5$ represents a linear or branched fatty acid residue containing from 1 to 40 carbon atoms and $R_6$ represents an in particular branched hydrocarbon-based chain containing from 1 to 40 carbon atoms, on condition that $R_5+R_6 \geq 10$, such as, for example, purcellin oil (cetostearyl octanoate), isononyl isononanoate, $C_{12}-C_{15}$ alkyl benzoate, isopropyl myristate, 2-ethylhexyl palmitate, isostearyl isostearate, and alkyl or polyalkyl octanoates, decanoates or ricinoleates; hydroxylated esters such as isostearyl lactate and diisostearyl malate; and pentaerythritol esters;
synthetic ethers containing from 10 to 40 carbon atoms;
$C_8$ to $C_{26}$ fatty alcohols such as oleyl alcohol;
mixtures thereof.

The additional apolar oils according to the invention are, in particular, silicone oils such as volatile or non-volatile, linear or cyclic polydimethylsiloxanes (PDMSs) that are liquid at room temperature; polydimethylsiloxanes comprising alkyl, alkoxy or phenyl groups which are pendent and/or at the end of the silicone chain, the groups each containing from 2 to 24 carbon atoms; phenylsilicones such as phenyl trimethicones, phenyl dimethicones, phenyl trimethylsiloxy diphenylsiloxanes, diphenyl dimethicones, diphenyl methyldiphenyl trisiloxanes and 2-phenylethyl trimethylsiloxysilicates; linear or branched hydrocarbons of synthetic or mineral origin, such as volatile or non-volatile liquid paraffins and derivatives thereof, petroleum jelly, liquid lanolin, polydecenes, hydrogenated polyisobutene such as parleam, and squalane, and mixtures thereof.

The additional oils are preferably apolar oils and more especially an oil or a mixture of oils of the hydrocarbon-based type of mineral or synthetic origin, chosen in particular from hydrocarbons, especially alkanes such as parleam oil, isoparaffins such as isododecane, and squalane, and mixtures thereof. These oils are advantageously combined with one or more phenylsilicone oils.

The liquid fatty phase preferably contains at least one additional non-volatile oil chosen in particular from hydrocarbon-based oils of mineral, plant or synthetic origin, synthetic esters or ethers and silicone oils, and mixtures thereof.

In practice, the total liquid fatty phase represents from 5% to 99% of the total weight of the composition, preferably from 20% to 75%.

The liquid fatty phase of the composition according to the invention also contains at least one additional volatile solvent, other than the fluoro oils described above, namely one or more volatile solvents.

For the purposes of the invention, the expression "volatile solvent" means any non-aqueous medium capable of evaporating on contact with the skin or the lips in less than one hour at room temperature and atmospheric pressure. The volatile solvent(s) of the invention is(are) organic solvents and in particular volatile cosmetic oils that are liquid at room temperature, having a non-zero vapour pressure, at room temperature and atmospheric pressure, ranging in particular from $10^{-3}$ to 300 mmHg (0.013 Pa to 40 000 Pa) and preferably greater than 0.3 mmHg (30 Pa).

According to the invention, these volatile solvents facilitate, in particular, the application of the composition to the skin, the lips or the integuments. These solvents may be hydrocarbon-based solvents, silicone solvents optionally comprising alkyl or alkoxy groups that are pendent or at the end of a silicone chain, or a mixture of these solvents. Preferably, these solvents are not alcohols containing at least 7 carbon atoms.

As volatile solvents which can be used in the invention, mention may be made of linear or cyclic silicone oils having a viscosity at room temperature of less than 8 cSt and in particular containing from 2 to 7 silicon atoms, these silicones optionally comprising alkyl or alkoxy groups containing from 1 to 10 carbon atoms. As volatile silicone oils which may be used in the invention, mention may be made in particular of octamethylcyclotetrasiloxane, decamethylcyclopenta-siloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

As other volatile solvents which may be used in the invention, mention may be made of hydrocarbon-based volatile oils containing from 8 to 16 carbon atoms, and mixtures thereof, and in particular branched $C_8$–$C_{16}$ alkanes such as $C_8$–$C_{16}$ isoalkanes (also known as isoparaffins), isododecane, isodecane, isohexadecane and, for example, the oils sold under the trade names "Isopars" or "Permetyls", and branched $C_8$–$C_{16}$ esters such as isohexyl neopentanoate, and mixtures thereof. The volatile solvent is preferably chosen from hydrocarbon-based volatile oils containing from 8 to 16 carbon atoms, and mixtures thereof.

Isododecane (Permetyls 99 A) and $C_8$–$C_{16}$ isoparaffins (Isopars L, E, H) and mixtures thereof, optionally combined with decamethyltetrasiloxane, are preferably used.

The additional oils, especially the additional volatile oils, in particular represent a content by mass of from 5% to 97.5% relative to the total weight of the composition, preferably from 10% to 75% and better still from 15% to 45%. In general, the amount of volatile solvent used is an amount which is sufficient to obtain transfer-resistance properties. This amount will be adapted by a person skilled in the art according to the desired intensity of the transfer-resistance properties.

The composition of the invention can also comprise any additive usually used in the field under consideration, chosen in particular from dyestuffs, antioxidants, essential oils, preserving agents, fragrances, fillers, waxes, products that are pasty at room temperature, neutralizers, polymers that are liposoluble or dispersible in the medium, cosmetic or dermatological active agents such as, for example, emollients, moisturizers, vitamins, essential fatty acids, sunscreens, dispersants such as poly(12-hydroxystearic acid), and mixtures thereof. These additives may be present in the composition in a proportion of from 0% to 20% (in particular from 0.01% to 20%) relative to the total weight of the composition and better still from 0.01% to 10%. The composition advantageously contains at least one cosmetic or dermatological active agent.

The composition of the invention can also contain, as additive, an aqueous phase containing water that is optionally thickened or gelled with an aqueous-phase thickener or gelling agent and optionally water-miscible compounds.

Needless to say, a person skilled in the art will take care to select the optional additional additives and/or the amount thereof such that the advantageous properties of the composition according to the invention are not, or are not substantially, adversely affected by the envisaged addition.

The composition according to the invention can be in the form of a tinted dermatological or care composition for keratin materials such as the skin, the lips and/or the integuments, in the form of an antisun composition or body hygiene composition in particular in the form of a deodorant product or make-up-removing product in stick form. It can be used in particular as a care base for the skin, integuments or the lips (lip balms, for protecting the lips against cold and/or sunlight and/or the wind, or care cream for the skin, the nails or the hair).

The composition of the invention may also be in the form of a coloured make-up product for the skin, in particular a foundation, optionally having care or treatment properties, a blusher, a face powder, an eye shadow, a concealer product, an eyeliner, a make-up product for the body; a make-up product for the lips such as a lipstick, optionally having care or treatment properties; a make-up product for integuments such as the nails or the eyelashes, in particular in the form of a mascara cake, or for the eyebrows and the hair, in particular in the form of a pencil.

Needless to say, the composition of the invention should be cosmetically or dermatologically acceptable, i.e. it should contain a non-toxic physiologically acceptable medium which should be able to be applied to the skin, integuments or the lips of human beings. For the purposes of the invention, the expression "cosmetically acceptable" means a composition of pleasant appearance, odour and feel.

The composition advantageously contains at least one cosmetic active agent and/or one dermatological active agent and/or at least one dyestuff. By means of the combination of at least one volatile solvent and of at least one polymer with an average molecular mass of less than or equal to 100 000, as defined above, trapping of the active agents and dyestuffs present in the composition is obtained, making it possible to keep them where they were applied, i.e. on the lips, the skin or integuments such as keratin fibres, after the volatile solvent(s) has(have) evaporated off, and to limit their transfer or redeposition onto a support other than the one to which they were applied.

The dyestuff according to the invention may be chosen from the lipophilic dyes, hydrophilic dyes, pigments and nacres usually used in cosmetic or dermatological compositions, and mixtures thereof. This dyestuff is generally present in a proportion of from 0.01% to 50% of the total weight of the composition, preferably from 5% to 30%, if it is present.

The liposoluble dyes are, for example, Sudan Red, D&C Red 17, D&C Green 6, β-carotene, soybean oil, Sudan Brown, D&C Yellow 11, D&C Violet 2, D&C Orange 5, quinoline yellow or methyl yellow. They can represent from 0.1% to 20% of the weight of the composition and better still from 0.1% to 6%.

The pigments may be white or coloured, mineral and/or organic, and coated or uncoated. Among the mineral pigments which may be mentioned are titanium dioxide, optionally surface-treated, zirconium oxide or cerium oxide, as well as iron oxide, chromium oxide, manganese violet, ultramarine blue, chromium hydrate and ferric blue. Among the organic pigments which may be mentioned are carbon black, pigments of D&C type, and lakes based on cochineal carmine or on barium, strontium, calcium or aluminium. The pigments can represent from 0.1% to 50% and better still from 2% to 30% of the total weight of the composition, if they are present.

The nacreous pigments may be chosen from white nacreous pigments such as mica coated with titanium or with bismuth oxychloride, coloured nacreous pigments such as titanium mica with iron oxides, titanium mica with, in particular, ferric blue or chromium oxide, titanium mica with an organic pigment of the type mentioned above, as well as nacreous pigments based on bismuth oxychloride. They can represent from 0.1% to 20% relative to the total weight of the composition, and better still from 0.1% to 15%, if they are present.

The composition can optionally contain one or more waxes to improve the structuring in stick form, although this rigid form can be obtained in the absence of wax. For the purposes of the present invention, a wax is a lipophilic fatty compound that is solid at room temperature (25° C.), which undergoes a reversible solid/liquid change of state, having a melting point of greater than 40° C. which may be up to 200° C., and having an anisotropic crystal organization in the solid state. The size of the crystals is such that the crystals diffract and/or scatter light, giving the composition a cloudy, more or less opaque appearance. By bringing the wax to its melting point, it is possible to make it miscible with oils and to form a microscopically homogeneous mixture, but, on returning the temperature of the mixture to room temperature, recrystallization of the wax in the oils of the mixture is obtained. It is this recrystallization in the mixture which is responsible for the reduction in the gloss of the said mixture. Thus, the composition advantageously contains little or no wax, and in particular less than 5% wax.

For the purposes of the application, the waxes are those generally used in cosmetics and dermatology; they are especially of natural origin, for instance beeswax, carnauba wax, candelilla wax, ouricury wax, Japan wax, cork fibre wax, sugar cane wax, paraffin wax, lignite wax, microcrystalline waxes, lanolin wax, montan wax, ozokerites and hydrogenated oils such as hydrogenated jojoba oil as well as waxes of synthetic origin, for instance polyethylene waxes derived from the polymerization of ethylene, waxes obtained by Fischer-Tropsch synthesis, fatty acid esters and glycerides that are solid at 40° C., silicone waxes such as alkyl- and alkoxy-poly(di)methylsiloxanes and/or poly(di)methylsiloxane esters that are solid at 40° C.

The composition of the invention also advantageously contains at least one polymer that is liposoluble or dispersible in the medium, especially having an average molecular weight of from 500 to 1 000 000 and better still from 5 000 to 15 000. This (these) liposoluble polymer(s) contribute(s) in particular towards increasing the viscosity and/or improving the staying power of the film. These liposoluble polymers advantageously have a softening point of not more than 30° C.

As examples of liposoluble polymers which can be used in the invention, mention may be made of: polyalkylenes, in particular polybutene, poly(meth)acrylates, alkylcelluloses with a linear or branched, saturated or unsaturated $C_1$ to $C_8$ alkyl radical, such as ethylcellulose and propylcellulose, silicone polymers that are compatible with the fatty phase, as well as vinylpyrrolidone (VP) copolymers, and mixtures thereof.

Vinylpyrrolidone copolymers, copolymers of a $C_2$ to $C_{30}$ and better still $C_3$ to $C_{22}$ alkene, and combinations thereof, are preferably used. As examples of VP copolymers which can be used in the invention, mention may be made of VP/vinyl acetate, VP/ethyl methacrylate, butylated polyvinylpyrrolidone (PVP), VP/ethyl methacrylate/methacrylic acid, VP/eicosene, VP/hexadecene, VP/triacontene, VP/styrene or VP/acrylic acid/lauryl methacrylate copolymer.

Preferably, not only for the staying power properties but also the feel and consistency properties of the film, the PVP/hexadecene copolymer having an average molecular weight of from 7 000 to 7 500 or alternatively the PVP/eicosene having an average molecular weight of from 8 000 to 9 000 is used.

The polymers that are liposoluble or dispersible in the composition of the invention are advantageously used in an amount of from 0.01% to 20% (as active material) relative to the total weight of the composition and better still from 1% to 10%, if they are present.

The composition according to the invention also advantageously contains at least one fatty compound that is pasty at room temperature. For the purposes of the invention, the expression "pasty fatty substance" means fatty substances with a melting point ranging from 20° C. to 55° C., preferably 25° C. to 45° C., and/or a viscosity at 40° C. ranging from 0.1 to 40 Pa.s (1 to 400 poises), preferably 0.5 to 25 Pa.s, measured using a Contraves TV or Rhéomat 80 viscometer, equipped with a spindle rotating at 60 Hz. A person skilled in the art can select the spindle for measuring the viscosity from the spindles MS-r3 and MS-r4, on the basis of his general knowledge, so as to be able to carry out the measurement of the pasty compound tested.

According to the invention, one or more pasty fatty substances are used. These fatty substances are preferably hydrocarbon-based compounds, optionally of polymeric type; they can also be chosen from silicone compounds and/or fluoro compounds; they may also be in the form of a mixture of hydrocarbon-based compounds and/or silicone compounds and/or fluoro compounds. In the case of a mixture of different pasty fatty substances, the hydrocarbon-based pasty compounds are preferably used in major proportion.

Among the pasty compounds which may be used in the composition according to the invention, mention may be made of lanolins and lanolin derivatives such as acetylated lanolins or oxypropylenated lanolins, having a viscosity of from 18 to 21 Pa.s, preferably 19 to 20.5 Pa.s, and/or a melting point of from 30° C. to 55° C., and mixtures thereof. It is also possible to use esters of fatty acids or of fatty alcohols, in particular those containing from 20 to 65 carbon atoms (melting point of about from 20° C. to 35° C. and/or viscosity at 40° C. ranging from 0.1 to 40 Pa.s), such as triisostearyl citrate or cetyl citrate; arachidyl propionate; polyvinyl laurate; cholesterol esters, such as triglycerides of plant origin, such as hydrogenated plant oils, viscous polyesters such as poly(12-hydroxystearic acid), and mixtures thereof. Triglycerides of plant origin which may be used are hydrogenated castor oil derivatives, such as "Thixinr" from Rheox.

Mention may also be made of pasty silicone fatty substances such as polydimethylsiloxanes (PDMSs) containing pendent chains of the alkyl or alkoxy type containing from 8 to 24 carbon atoms, and having a melting point of 20–55° C., such as stearyldimethicones, in particular those sold by Dow Corning under the trade names DC2503 and DC25514, and mixtures thereof.

The pasty fatty substance(s) may be present in a proportion of from 0.1% to 60% by weight, relative to the total weight of the composition, preferably in a proportion of from 1–45% by weight, and even more preferably in a proportion of from 2–30% by weight, in the composition, if they are present.

The composition according to the invention may be manufactured by the known processes, that are generally used in cosmetics or dermatology. It may be manufactured by the process which consists in heating the polymer at least to its softening point, in adding the amphiphilic compound(s), the dyestuffs and the additives thereto and then in mixing everything together until a clear, transparent solution is obtained. After reducing the temperature, the volatile solvent(s) is(are) then added to the mixture obtained. The homogeneous mixture obtained can then be cast in a suitable mould such as a lipstick mould or directly into the packaging articles (case or dish in particular).

A subject of the invention is also a lipstick composition in stick form containing at least one continuous liquid fatty phase comprising at least one fluoro oil, the liquid fatty phase being structured with at least one non-waxy polymer giving the composition the appearance of an elastic deformable solid with a hardness ranging from 30 to 300 g (measured according to the cheese wire method described above), in the absence of wax.

This lipstick composition in stick form advantageously contains an additive chosen from fatty compounds that are pasty at room temperature, liposoluble polymers and mixtures thereof, as defined previously. The non-waxy polymer is preferably a polymer whose skeleton comprises hydrocarbon-based units containing a hetero atom, as defined previously.

A subject of the invention is also a cosmetic process for caring for, making up or treating human keratin materials, and in particular the skin, the lips and integuments, comprising the application to the keratin materials of the composition, in particular the cosmetic composition, as defined above.

A subject of the invention is also the use of the combination of at least one liquid fatty phase containing a fluoro oil and of at least one polymer with a weight-average molecular mass of less than or equal to 100 000, comprising a) a polymer skeleton containing hydrocarbon-based repeating units containing at least one hetero atom, and b) optionally pendent and/or terminal fatty chains that are optionally functionalized, containing from 6 to 120 carbon atoms and being linked to these hydrocarbon-based units, in a cosmetic composition or for the manufacture of a physiologically acceptable composition, in order to reduce the transfer and/or deposit of traces of a film of the said composition, applied to the keratin materials, onto a support placed in contact with the said film and/or to improve the staying power of the said film and/or to obtain a non-sticky film. This film is also glossy and/or comfortable.

The invention is illustrated in greater detail in the examples which follow. The percentages are given by weight.

EXAMPLE 1

Lipstick with the: which content and in which phase?

| Phase A | |
|---|---|
| Uniclear 100 | 18% |
| Fluorosilicone (X22819 from Shin Etsu) | 5% |
| Castor oil | 2% |
| Hydrogenated isoparaffin | 4% |
| Isononyl isononanoate | 4% |
| Phenyltrimethylsiloxytrisiloxane | 8% |
| Vinylpyrrolidone/1-eicosene copolymer | 2% |
| Phase B | |
| Pigments | 10% |
| Hydrogenated isoparaffin | 5% |
| Liquid lanolin | 5% |
| Poly(12-hydroxystearic acid) | 2% |
| Phase C | |
| Isododecane | 25% |
| Decamethyltetrasiloxane | 10% |

The pigment phase (B) is ground using a three-roll mill and introduced into the oily phase A preheated to 100° C., until the mixture is fully homogenized. The volatile phase C is then added to the above mixture, cooled to 85° C. The resulting mixture is left in contact for 10 min and then cast into lipstick moulds.

Applied to the lips, the lipstick forms a glossy, non-sticky film that has good transfer-resistance properties.

EXAMPLE 2

Lipstick

| Phase A | |
|---|---|
| Uniclear 100 | 18% |
| Castor oil | 8% |

| -continued | |
|---|---|
| Hydrogenated isoparaffin | 5% |
| Isononyl isononanoate | 5% |
| Phenyltrimethylsiloxytrisiloxane | 8% |
| Vinylpyrrolidone/1-eicosene copolymer | 2% |
| Phase B | |
| Pigments | 10% |
| Hydrogenated isoparaffin | 5% |
| Liquid lanolin | 5% |
| Poly(12-hydroxystearic acid) | 2% |
| Phase C | |
| Nonafluoromethoxybutane | 5% |
| Isododecane | 22% |
| Decamethyltetrasiloxane | 5% |

The pigment phase (B) is ground using a three-roll mill and introduced into the oily phase A preheated to 100° C., until the mixture is fully homogenized. The volatile phase C is then added to the above mixture, cooled to 85° C. The resulting mixture is left in contact for 10 min and then cast into lipstick moulds.

The lipstick obtained deposits a glossy, non-sticky and transfer-resistant film.

What is claimed is:

1. A composition comprising at least one liquid fatty phase which comprises at least one fluoro oil, wherein the at least one liquid fatty phase is structured with at least one structuring polymer chosen from polyamide polymers of formula (I):

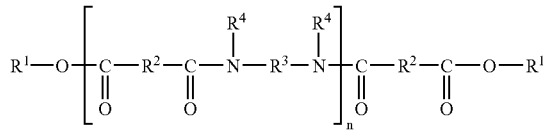

in which:

n is an integer which represents the number of amide units such that the number of ester groups present in said at least one polyamide polymer ranges from 10% to 50% of the total number of all ester groups and all amide groups comprised in said at least one polyamide polymer;

$R^1$ is independently chosen from alkyl and alkenyl groups containing at least 4 carbon atoms;

$R^2$ is independently chosen from $C_4$ to $C_{42}$ hydrocarbon-based groups, wherein 50% of the $R^2$ groups are chosen from $C_{30}$ to $C_{42}$ hydrocarbon-based groups;

$R^3$ is independently chosen from organic groups containing at least 2 carbon atoms, hydrogen, and optionally at least one atom chosen from oxygen and nitrogen atoms; and $R^4$ is independently chosen from hydrogen and $C_1$ to $C_{10}$ alkyl groups, wherein at least 50% of the $R^4$ groups are hydrogen.

2. The composition according to claim 1, wherein said at least one structuring polymer is present in the composition in an amount ranging from 0.5% to 80% by weight relative to the total weight of the composition.

3. The composition according to claim 1, wherein the at least one fluoro oil is chosen from fluorosilicone compounds of formula (II):

$$R_1-Si(R_1)(R_1)-O-[Si(R_1)(R_1)-O]_m-[Si(CH_3)(R)(Rf)-O]_n-Si(R_1)(R_1)-R_1 \quad (II)$$

wherein:
R is chosen from linear and branched divalent alkyl groups containing from 1 to 6 carbon atoms;
Rf is a fluoroalkyl radical with from 1 to 9 carbon atoms;
$R_1$ is independently chosen from $C_1$–$C_{20}$ alkyl radicals, hydroxyl radicals, and phenyl radicals;
m ranges from 0 to 150; and
n ranges from 1 to 300.

4. The composition according to claim 1, wherein the at least one fluoro oil is chosen from fluorosilicone compounds of formula (III) below:

$$H_3C-Si(CH_3)(CH_3)-O-[Si(CH_3)(CH_3)-O]_m-[Si(CH_3)(R)(CF_3)-O]_n-Si(CH_3)(CH_3)-CH_3 \quad (III)$$

wherein:
R is chosen from divalent methyl, ethyl, propyl, and butyl groups;
m ranges from 0 to 80; and
n ranges from 1 to 30.

5. The composition according to claim 1, wherein the at least one fluoro oil is chosen from perfluorocycloalkyls of formula (IV):

$$(CF_2)_n \quad [CF-(CF_2)_p-F]_m \quad (IV)$$

wherein:
n is equal to 4 or 5;
m is equal to 1 or 2; and
p ranges from 1 to 3;
with the proviso that when m=2, the $(CF_2)_p$—F groups are not necessarily alpha to each other.

6. The composition according to claim 1, wherein the at least one fluoro oil is chosen from fluoroalkyl and heterofluoroalkyl compounds of formula (V):

$$CH_3-(CH_2)_n-[Z]_t-X-CF_3 \quad (V)$$

wherein:
t is 0 or 1;
n ranges from 0 to 3;
X is chosen from linear and branched divalent perfluoroalkyl radicals with from 2 to 5 carbon atoms; and
Z is chosen from O, S, or NR, R being hydrogen, a radical —$(CH_2)_n$—$CH_3$, wherein n is defined as above, or —$(CF_2)_m$—$CF_3$, wherein m ranges from 2 to 5.

7. The composition according to claim 1, wherein the at least one fluoro oil is chosen from perfluoroalkane compounds of formula (VI):

$$CF_3-(CF_2)_n-CF_3 \quad (VI)$$

wherein n ranges from 2 to 6.

8. The composition according to claim 1, wherein the at least one fluoro oil is chosen from perfluoromorpholine derivatives of formula (VII):

$$\text{(morpholine ring with R, } F_2C, CF_2, F_2C, CF_2, O\text{)} \quad (VII)$$

wherein R is chosen from $C_1$–$C_4$ perfluoroalkyl radicals.

9. The composition according to claim 1, wherein the at least one fluoro oil is chosen from the perfluompolyethers of formulae (VIII) and (IX):

$$F-[CF(CF_3)-CF_2-O]_n-CF_2-CF_3 \quad (VIII)$$

wherein n ranges from 7 to 30; and $$CF_3-[O-CF(CF_3)-CF_2]_m-[O-CF_2]_p-OCF_3 \quad (IX)$$

wherein the ratio m/p ranges from 20 to 40, and the molecular weight ranges from 500 to 20,000.

10. The composition according to claim 1, wherein the at least one fluoro oil is chosen from fluorosilicone compounds of formula (X):

$$CF_3-(CF_2)_k-(CH_2)_l-O-C(O)-N(R_1)-(CH_2)_p-Si(R_2)-O-[Si(R_2)_3]_2 \quad (X)$$

wherein:
k ranges from 1 to 17;
l ranges from 1 to 18;
p ranges from 1 to 6;
$R_1$ is chosen from hydrogen and $C_1$–$C_6$ alkyl radicals;
$R_2$ Is chosen from $C_1$–$C_6$ alkyl radicals and —$OSi(R_3)_3$, $R_3$ being chosen from $C_1$–$C_4$ alkyl radicals.

11. The composition according to claim 1, wherein the at least one fluoro oil is chosen from fluoroalkylsilicones of formula (XI):

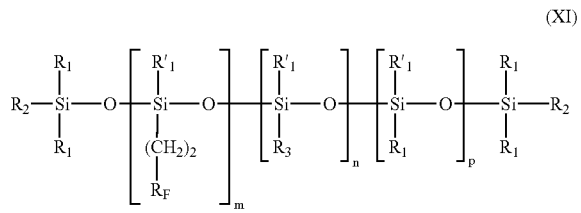

(XI)

wherein:
$R_1$ and $R'_1$ are independently chosen from linear and branched alkyl radicals with from 1 to 6 carbon atoms, and phenyl radicals;
$R_2$ is chosen from $R_1$, —OH, and —$(CH_2)_f$—$R_F$, f being an integer ranging from 0 to 10;
$R_3$ is chosen from linear and branched alkyl radicals with from 6 to 22 carbon atoms;
$R_F$ is chosen from —$(CF_2)_q$—$CF_3$, q being an integer ranging from 0 to 10;
m and n are independently chosen from an integer ranging from 1 to 50; and
p is an integer ranging from 0 to 2,000.

12. The composition according to claim 1, wherein the at least one fluoro oil is chosen from fluoroalkylsilicones of formula (XII):

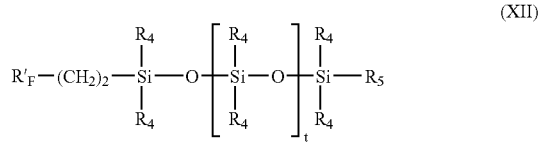

(XII)

wherein:
$R_4$ is chosen from linear and branched alkyl radicals with from 1 to 6 carbon atoms, and phenyl radicals;
$R_5$ is chosen from linear and branched alkyl radicals with from 6 to 22 carbon atoms, and phenyl radicals;
$R'_F$ is chosen from —$(CF_2)_s$—$CF_3$, wherein s is an integer ranging from 0 to 15; and
t is an integer ranging from 1 to 2,000.

13. The composition according to claim 1, wherein the at least one fluoro oil is present in an amount ranging from 0.1% to 50% by weight, relative to the total weight of the composition.

14. The composition according to claim 1, further comprising at least one additional oil, other than the said at least one fluoro oil.

15. The composition according to claim 1, wherein said at least one liquid fatty phase further comprises one additional oil, said additional oil being chosen from non-volatile oil.

16. The composition according to claim 1, further comprising at least one volatile solvent.

17. The composition according to claim 1, wherein the at least one liquid fatty phase further comprises an apolar oil.

18. The composition according to claim 1, wherein the at least one liquid fatty phase is present in an amount ranging from 5% to 99% by weight, relative to the total weight of the composition.

19. The composition according to claim 1, further comprising at least one dyestuff.

20. The composition according to claim 1, further comprising at least one additive chosen from water, antioxidants, essential oils, preserving agents, fragrances, fillers, waxes, fatty compounds that are pasty at room temperature, neutralizers, polymers that are liposoluble or dispersible in the physiologically acceptable medium, cosmetic agents, dermatological active agents, and dispersants.

21. The composition according to claim 1, wherein the composition is in the form of a rigid gel or stick.

22. The composition according to claim 1, wherein the composition is a cosmetic composition chosen from mascara, eyeliner, a foundation, a lipstick, a blusher, a deodorant product, a make-up-removing product, a body make-up product, an eye shadow, a face powder, a concealer product, a shampoo, a conditioner, an antisun product, a bodycare product, a facial care product, or a nail varnish.

23. A process for caring for, making up, or treating a keratin material, comprising the application to the keratin material of a cosmetic composition comprising at least one liquid fatty phase which comprises at least one fluoro oil, wherein the at least one liquid fatty phase is structured with at least one structuring polymer chosen from polyamide polymers of formula (I):

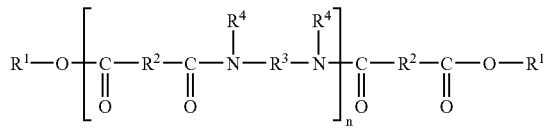

in which:
n is an integer which represents the number of amide units such that the number of ester groups present in said at least one polyamide polymer ranges from 10% to 50% of the total number of all ester groups and all amide groups comprised in said at least one polyamide polymer;
$R^1$ is independently chosen from alkyl and alkenyl groups with at least 4 carbon atoms;
$R^2$ is independently chosen from $C_4$ to $C_{42}$ hydrocarbon-based groups, wherein 50% of the $R^2$ groups are chosen from $C_{30}$ to $C_{42}$ hydrocarbon-based groups;
$R^3$ is independently chosen from organic groups with at least 2 carbon atoms, hydrogen; and
$R^4$ is independently chosen from hydrogen and $C_1$ to $C_{10}$ alkyl groups, wherein at least 50% of the $R^4$ groups are hydrogen
wherein the at least one liquid fatty phase and the at least one polyamide polymer form a physiologically acceptable medium.

* * * * *

UNITED STATES PATENT AND TRADEMARK OFFICE
CERTIFICATE OF CORRECTION

PATENT NO. : 7,052,681 B2  
APPLICATION NO. : 10/047987  
DATED : May 30, 2006  
INVENTOR(S) : Veronique Ferrari It is certified that error appears in the above-identified patent and that said Letters Patent is hereby corrected as shown below:

In claim 1, column 18, line 51, "containing" should read --with--.

In claim 1, column 18, lines 56-57, "containing" should read --with--.

In claim 1, column 18, lines 57-58, delete ", and optionally at least one atom chosen from oxygen and nitrogen atoms".

In claim 3, column 19, line 16, "containing" should read --with--.

In claim 9, column 20, line 29, "perfluompolyethers" should read --perfluoropolyethers--.

In claim 10, column 20, line 66, "Is" should read --is--.

In claim 15, column 21, line 56, "non-volatile oil." should read --non-volatile oils.--.

Signed and Sealed this

Nineteenth Day of September, 2006

JON W. DUDAS  
*Director of the United States Patent and Trademark Office*